United States Patent
Guo et al.

(10) Patent No.: US 11,701,232 B2
(45) Date of Patent: Jul. 18, 2023

(54) ACELLULAR BIOACTIVE SCAFFOLD DEVICE AND METHODS OF FABRICATION AND TREATMENT RELATING THERETO

(71) Applicant: University of Maryland, College Park, College Park, MD (US)

(72) Inventors: Ting Guo, Cambridge, MA (US); John Patrick Fisher, Kensington, MD (US); Hannah Baker, Baltimore, MD (US); Max Jonah Lerman, Silver Spring, MD (US); Robert Choe, Arlington, VA (US)

(73) Assignee: University of Maryland, College Park, College Park, MD (US)

( * ) Notice: Subject to any disclaimer, the term of this patent is extended or adjusted under 35 U.S.C. 154(b) by 388 days.

(21) Appl. No.: 16/743,315

(22) Filed: Jan. 15, 2020

(65) Prior Publication Data
US 2020/0222190 A1    Jul. 16, 2020

Related U.S. Application Data

(60) Provisional application No. 62/828,303, filed on Apr. 2, 2019, provisional application No. 62/792,722, filed on Jan. 15, 2019.

(51) Int. Cl.
*A61F 2/30* (2006.01)
*A61L 27/18* (2006.01)

(52) U.S. Cl.
CPC ......... *A61F 2/30756* (2013.01); *A61L 27/18* (2013.01); *A61F 2002/30766* (2013.01); *A61F 2002/30985* (2013.01)

(58) Field of Classification Search
CPC ........ A61F 2/30756; A61F 2002/30766; A61F 2002/30985; A61F 2/3094; A61L 27/18;
(Continued)

(56) References Cited

U.S. PATENT DOCUMENTS 7,148,209 B2    12/2006 Hoemann et al.
2002/0005600 A1*   1/2002 Ma ................... G01N 30/482
                                                        521/84.1
(Continued)

FOREIGN PATENT DOCUMENTS

CN          103877616 A      6/2014
WO     WO 2003/000480 A1    1/2003
(Continued)

OTHER PUBLICATIONS

Aae, T. F et al. (2018) "Microfracture Is More Cost-Effective Than Autologous Chondrocyte Implantation: A Review of Level 1 And Level 2 Studies With 5 Year Follow-Up," Knee Surgery, Sport. Traumatol. Arthrosc. Doi:10.1007/S00167-017-4802-5.
(Continued)

*Primary Examiner* — Yashita Sharma
(74) *Attorney, Agent, or Firm* — Jeffrey I. Auerbach; Auerbach, LLC

(57) ABSTRACT

An implantable acellular polymeric scaffold device functionalized with aggrecan is provided. Also provided are methods of fabricating a polymeric scaffold device, including methods of fabricating the scaffold device via 3D printing. Methods of treating a cartilage defect in a subject in need thereof comprise application of the disclosed scaffold device in combination with microfracture procedures. A specialized lid for a centrifugation well plate is also provided.

10 Claims, 20 Drawing Sheets
(3 of 20 Drawing Sheet(s) Filed in Color)

(A)

SZ  Parallel pattern
    0.2 mm fiber spacing
    0° offset between layers

MZ  Crosshatch pattern
    0.4 mm fiber spacing
    90° layer-layer offset
    ±45° layer-contour offset DZ  Perpendicular pattern
    0.2 mm fiber spacing
    90° layer-layer offset

(58) Field of Classification Search
CPC ......... A61L 2300/252; A61L 2300/412; B33Y 80/00
See application file for complete search history.

(56) References Cited

U.S. PATENT DOCUMENTS

| | | | |
|---|---|---|---|
| 2004/0078090 A1 | 4/2004 | Binette et al. | |
| 2005/0187146 A1 | 8/2005 | Helmus et al. | |
| 2006/0111778 A1 | 5/2006 | Michalow | |
| 2010/0233234 A1 | 9/2010 | Arinzeh et al. | |
| 2011/0166417 A1* | 7/2011 | Lin | F01N 13/08 514/8.8 |
| 2011/0177135 A1 | 7/2011 | Rueger et al. | |
| 2012/0100185 A1 | 4/2012 | Wen et al. | |
| 2012/0165957 A1* | 6/2012 | Everland | A61L 27/54 623/23.72 |
| 2016/0067375 A1 | 3/2016 | Holmes et al. | |
| 2016/0302911 A1* | 10/2016 | Soletti | A61F 2/06 |
| 2017/0143831 A1 | 5/2017 | Varanasi et al. | |
| 2018/0085493 A1 | 3/2018 | Lee | |
| 2018/0256780 A1* | 9/2018 | Jabbari | A61K 47/58 |

FOREIGN PATENT DOCUMENTS

| | | |
|---|---|---|
| WO | WO 2009/045176 A1 | 4/2009 |
| WO | WO 2017/214736 A1 | 12/2017 |

OTHER PUBLICATIONS

Athanasiou, K.A. et al. (1991) "*Interspecies Comparisons of in Situ Intrinsic Mechanical Properties of Distal Femoral Cartilage*," J Orthop Res 9(3):330-40.
Bae, D. et al. (2006) "*Cartilage Healing After Microfracture in Osteoarthritic Knees*," Arthroscopy—The Journal of Arthroscopic and Related Surgery 22(4):367-374 (Abstract Only).
Basso, D. et al. (1995) "*A Sensitive And Reliable Locomotor Rating-Scale for Open-Field Testing in Rats*," Journal of Neurotrauma 12(1):1-21 (Abstract Only).
Beck, A., et al. "*Treatment of Articular Cartilage Defects With Microfracture And Autologous Matrix-Induced Chondrogenesis Leads to Extensive Subchondral Bone Cyst Formation in a Sheep Model*," Am. J. Sports Med. (2016).
Cao, L. et al. (1998) "*Expression of the G1 Domain of Aggrecan Interferes With Chondrocyte Attachment and Adhesion*," Matrix Biol 17(5):379-92.
Cao, L. et al. (1999) "*Chondrocyte Apoptosis Induced by Aggrecan G1 Domain as a Result of Decreased Cell Adhesion*," Exp Cell Res 246(2):527-37.
Cengiz, I. F. et al. (2018) "*Orthopaedic Regenerative Tissue Engineering En Route to the Holy Grail: Disequilibrium Between the Demand and the Supply in the Operating Room*," Journal of Experimental Orthopaedics 5.
Chu, C.R. et al. (2010) "*Animal Models for Cartilage Regeneration and Repair*," Tissue Eng Part B Rev 16(1):105-15.
Coates, E. E. & Fisher, J. P. In Biomaterials for Tissue Engineering 279-306 (2011). Doi: 10.1007/978-3-7091-0385-2.
Coates, E. E. et al. (2010) "*Phenotypic Variations in Chondrocyte Subpopulations and Their Response Toin Vitro Culture and External Stimuli*," Annals of Biomedical Engineering 38, 3371-3388.
Cohen, N. et al. (1998) "*Composition and Dynamics of Articular Cartilage: Structure, Function, and Maintaining Healthy State*," J Ortho & Sports Phys Ther 28(4):203-215.
Deshpande, B.R. et al. (2016) "*Number of Persons With Symptomatic Knee Osteoarthritis in the US: Impact Of Race And Ethnicity, Age, Sex, and Obesity*," Arthritis Care Res 68(12):1743-1750.
Doral, M. N. et al. (2012) "*Treatment of Osteochondral Lesions of the Talus With Microfracture Technique and Postoperative Hyaluronan Injection*," Knee Surgery, Sport. Traumatol. Arthrosc. 20:1398-1403.

Drobnic, M. et al. (2006) "*Comparison of Four Techniques for the Fixation of a Collagen Scaffold in the Human Cadaveric Knee*," Osteoarthritis Cartilage 14(4):337-44.
Erggelet, C. et al. (2009) "*Formation of Cartilage Repair Tissue in Articular Cartilage Defects Pretreated With Microfracture and Covered With Cell-Free Polymer-Based Implants*," J Orthop Res 27(10):1353-60.
Ferlin, K.M. et al. "*Separation of Mesenchymal Stem Cells Through a Strategic Centrifugation Protocol*," Tissue Engineering Part C-Methods 22(4):348-359 (Abstract Only).
Fox, S. et al. (2009) "*The Basic Science of Articular Cartilage: Structure, Composition, and Function*," Sports Health 1(6), 461-8.
Frank, R. M. et al. (2018) "*Reoperation Rates After Cartilage Restoration Procedures In The Knee: Analysis of a Large US Commercial Database*," Am. J. Orthop 47(6).
Frisbie, D. et al. (2006) "*Effects of Calcified Cartilage on Healing of Chondral Defects Treated With Microfracture in Horses*," American Journal of Sports Medicine 34(11):1824-1831.
Gregory, M. H. et al. "*A Review of Translational Animal Models for Knee Osteoarthritis*," Arthritis (2012). Doi:10.1155/2012/764621.
Guo, T. et al. (2017) "*3D Printing PLGA: A Quantitative Examination of the Effects of Polymer Composition and Printing Parameters on Print Resolution*," Biofabrication 9(2):024101.
Guo, T. et al. (2017) "*Engineering Niches for Cartilage Tissue Regeneration*," In A. Vishwakarma, J. Karp (Eds.), Biology and Engineering of Stem Cell Niches, Elsevier.
Guo, T. et al. (2017) "*Three-Dimensional Printing Articular Cartilage: Recapitulating the Complexity of Native Tissue*," Tissue Engineering Part B—Reviews 23(3):225-236.
Guo, T. et al. (2018) "*3D Printed Biofunctionalized Scaffolds for Microfracture Repair of Cartilage Defects*," Biomaterials Doi:10.1016/J.Biomaterials 09.022.
Guo, T. et al. (2018) "*Three Dimensional Extrusion Printing Induces Polymer Molecule Alignment and Cell Organization Within Engineered Cartilage*," J Biomed Mater Res A 106(8):2190-2199.
Häger, C. et al. (2017) "*The Sheep Grimace Scale as an Indicator of Post-Operative Distress and Pain in Laboratory Sheep*," Plos One Doi:10.1371/Journal.Pone.0175839.
Han, C.W. et al. (2003) "*Analysis of Rabbit Articular Cartilage Repair After Chondrocyte Implantation Using Optical Coherence Tomography*," Osteoarthritis and Cartilage 11(2):111-121.
Hinckel, B.B. et al. (2017) "*Autologous Chondrocytes and Next-Generation Matrix-Based Autologous Chondrocyte Implantation*," Clin Sports Med 36(3):525-548 (Abstract Only).
Ho, S.T. et al. (2010) "*The Evaluation of a Biphasic Osteochondral Implant Coupled With an Electrospun Membrane in a Large Animal Model*," Tissue Eng Part A 16(4):1123-41 (Abstract Only).
Hoemann, C. D. et al. (2005) "*Chitosan-Glycerol Phosphate/Blood Implants Improve Hyaline Cartilage Repair in Ovine Microfracture Defects*," J. Bone Jt. Surg.—Ser. A 87:2671-2686 (Abstract Only).
Hoemann, C.D. et al. (2007) "*Chitosan-Glycerol Phosphate/Blood Implants Elicit Hyaline Cartilage Repair Integrated With Porous Subchondral Bone in Microdrilled Rabbit Defects*," Osteoarthritis Cartilage 15(1):78-89.
Hurst, J. et al. (2010) "*Rehabilitation Following Microfracture for Chondral Injury in the Knee*," Clinics in Sports Medicine 29(2):257 (Abstract Only).
Hwang, C.M. et al. (2008) "*Microfluidic Chip-Based Fabrication of PLGA Microfiber Scaffolds for Tissue Engineering*," Langmuir, 24,13, 6845-6851.
Jin, R. et al. (2010) "*Synthesis and Characterization of Hyaluronic Acid-Poly(Ethylene Glycol) Hydrogels via Michael Addition: An Injectable Biomaterial for Cartilage Repair*," Acta Biomater 6(6):1968-77.
Jung, Y. et al. (2008) "*Cartilage Regeneration With Highly-Elastic Three-Dimensional Scaffolds Prepared From Biodegradable Poly(L-Lactide-Co-Epsilon-Caprolactone)*," Biomaterials 29(35):4630-6.
Kang, S.-W. et al. (2008) "*Articular Cartilage Regeneration With Microfracture and Hyaluronic Acid*," Biotechnol. Lett. 30:435-9.
Kempson, G. E. (1982) "*Relationship Between the Tensile Properties of Articular Cartilage From the Human Knee and Age*," Ann. Rheum. Dis. 41, 508-511.

(56) References Cited

OTHER PUBLICATIONS

Kiani, C. et al. (2002) "Structure and Function of Aggrecan," Cell Res 12(1):19-32.

Koegler, W. et al. (2004) "Osteoblast Response to PLGA Tissue Engineering Scaffolds With PEO Modified Surface Chemistries and Demonstration of Patterned Cell Response," Biomaterials 25: 2819-2830.

Kon, E. et al. (2012) "ACI and MACI," J Knee Surgery 25(1):17-22 (Abstract Only).

La, W-G. et al. (2016) "Systemically Replicated Organic and Inorganic Bony Microenvironment for New Bone Formation Generated by a 3D Printing Technology," RSC Advances 6:11546.

Lawrence, R. et al. (2008) "Estimates of the Prevalence of Arthritis and Other Rheumatic Conditions in the United States," Arthritis and Rheumatism 58 (1) 26-35.

Mainil-Varlet, P. et al. (2001) "Articular Cartilage Repair Using a Tissue-Engineered Cartilage-Like Implant: an Animal Study," Osteoarthritis and Cartilage 9:S6-S15.

Mironov, V. et al. (2003) "Organ Printing: Computer-Aided Jet-Based 3D Tissue Engineering," Trends Biotechnol 21(4):157-61 (Abstract Only).

Mithoefer, K. et al. (2005) "The Microfracture Technique for the Treatment of Articular Cartilage Lesions in the Knee—a Prospective Cohort Study," Journal of Bone and Joint Surgery—American vol. 87A(9):1911-1920 (Abstract Only).

Mohan, N. et al. (2015) "Microsphere-Based Gradient Implants for Osteochondral Regeneration: A Long-Term Study in Sheep," Regen. Med. Doi:10.2217/Rme.15.38.

Nettles, D.L. et al. (2004) "Photocrosslinkable Hyaluronan as a Scaffold for Articular Cartilage Repair," Ann Biomed Eng 32(3):391-7 (Abstract Only).

Rogowska, J. et al. (2003) "Cartilage Thickness Measurements From Optical Coherence Tomography," J Optical Society of America A—Optics Image Science And Vision 20(2):357-367 (Abstract Only).

Rowland, D. et al. (2016) "A Comparative Evaluation of the Effect of Polymer Chemistry and Fiber Orientation on Mesenchymal Stem Cell Differentiation," The Authors Jnl of Biomedical Materials Res. A, vol. 104A:11 2843-2863.

Schmitz, N. et al. (2010) "Basic Methods in Histopathology of Joint Tissues," Osteoarthritis Cartilage 18 Suppl 3:S113-6.

Shao, X. et al. (2006) "Evaluation of a Hybrid Scaffold/Cell Construct in Repair of High-Load-Bearing Osteochondral Defects in Rabbits," Biomaterials 27(7):1071-80.

Shao, X. et al. (2006) "Repair of Large Articular Osteochondral Defects Using Hybrid Scaffolds and Bone Marrow-Derived Mesenchymal Stem Cells in a Rabbit Model," Tissue Eng 12(6):1539-51 (Abstract Only).

Shapiro, F. et al. (1993) "Cell Origin and Differentiation in the Repair of Full-Thickness Defects of Articular Cartilage," J Bone Joint Surg Am 75(4):532-53 (Abstract Only).

Steadman, J. et al. (2001) "Microfracture: Surgical Technique and Rehabilitation to Treat Chondral Defects," Clinical Orthopaedics and Related Research 391:S362-S369.

Steadman, J.R. et al. (2003) "Outcomes of Microfracture for Traumatic Chondral Defects of the Knee: Average 11-Year Follow-Up," Arthroscopy 19(5):477-84.

Steinwachs, M. R. et al. (2008) "Marrow Stimulation Techniques," Injury 39:26-31.

Tang, Q. et al. (2014) "Real-Time Epidural Anesthesia Guidance Using Optical Coherence Tomography Needle Probe," Quantitative Imaging in Medicine and Surgery 5(1):118-124.

Tang, Q. et al. (2016) "Depth-Resolved Imaging of Colon Tumor Using Optical Coherence Tomography and Fluorescence Laminar Optical Tomography," Biomedical Optics Express 7(12):5218-5232.

U.S. Food and Drug Administration: (2011) "Guidance for Industry—Preparation of Ides and Inds for Products Intended to Repair or Replace Knee Cartilage."

Xu, X. et al. (2017) "In Vivo Repair of Full-Thickness Cartilage Defect With Human Ipsc-Derived Mesenchymal Progenitor Cells in a Rabbit Model," Experimental and Therapeutic Medicine 14(1):239-245.

Yanagishita, M. (1993) "Function of Proteoglycans in the Extracellular-Matrix," Acta Pathologica Japonica 43(6):283-293 (Abstract Only).

Yang, B.B. et al. (1998) "Aggrecan and Link Protein Affect Cell Adhesion to Culture Plates and to Type II Collagen," Matrix Biol 16(9):541-61.

Yang, H.S. et al. (2011) "Hyaline Cartilage Regeneration by Combined Therapy of Microfracture and Long-Term Bone Morphogenetic Protein-2 Delivery," Tissue Engineering Part A, vol. 17:13,14 1809-1818.

Yoshii, S. et al. (2009) "Functional Restoration of Rabbit Spinal Cord Using Collagen-Filament Scaffold," J. Tissue Engineer. Regener. Med. 3(1): 19-25.

* cited by examiner

Figure 5 (cont.)
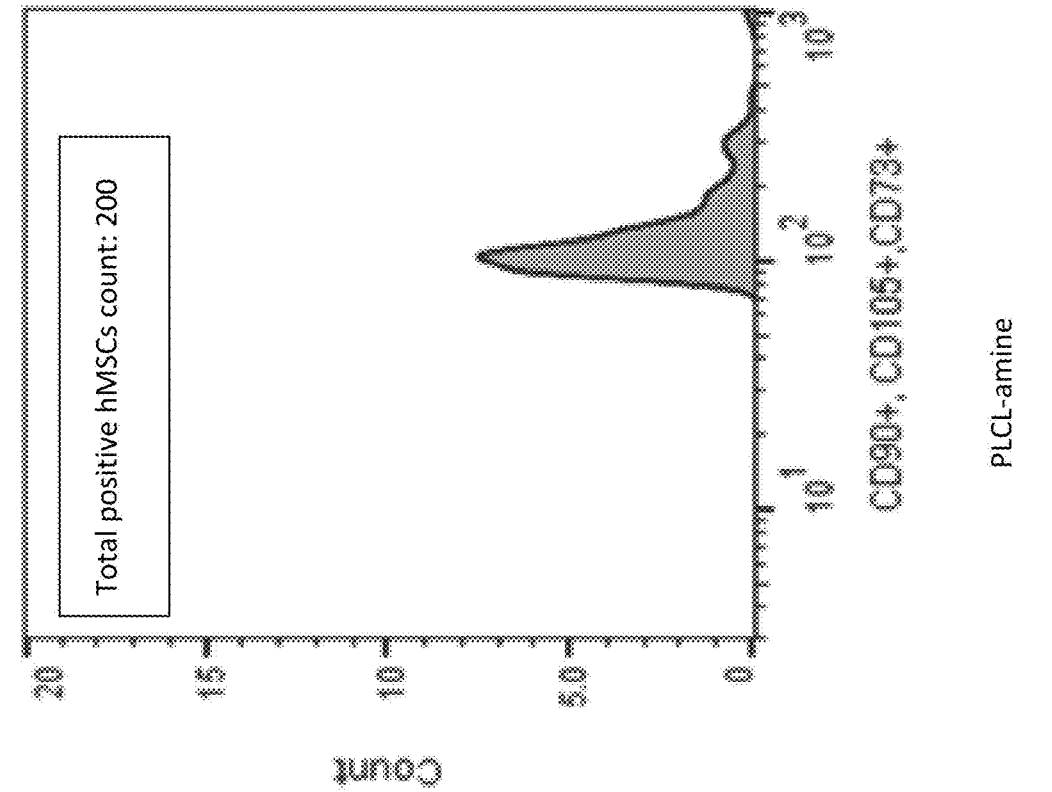
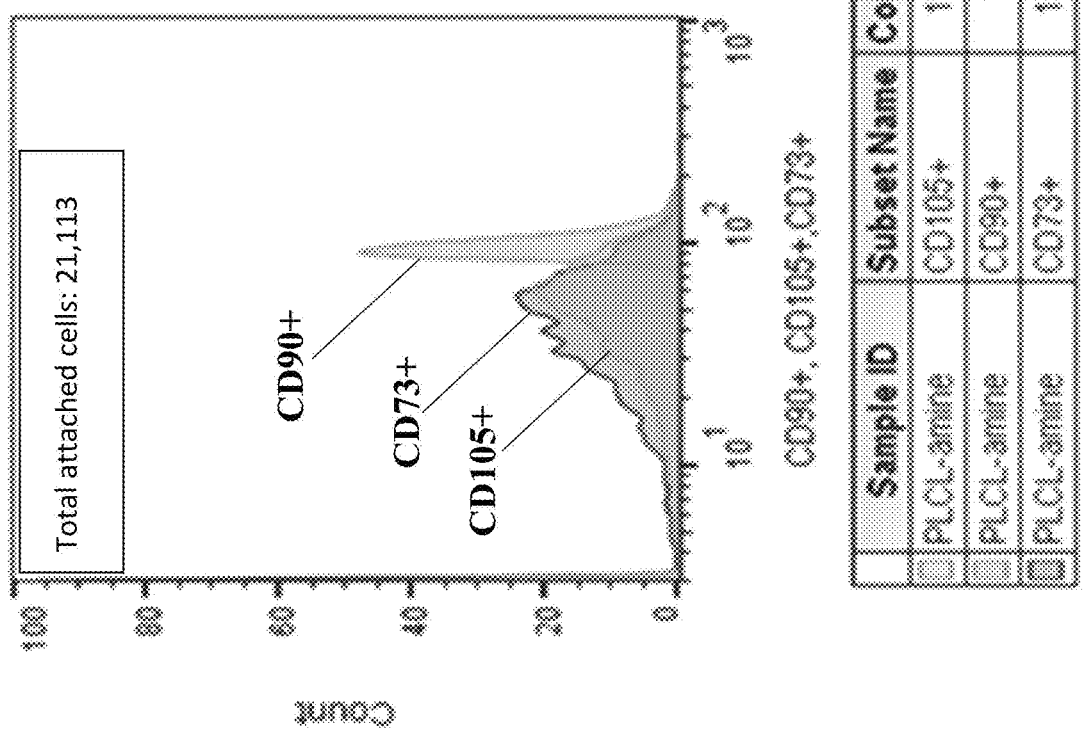

Figure 11
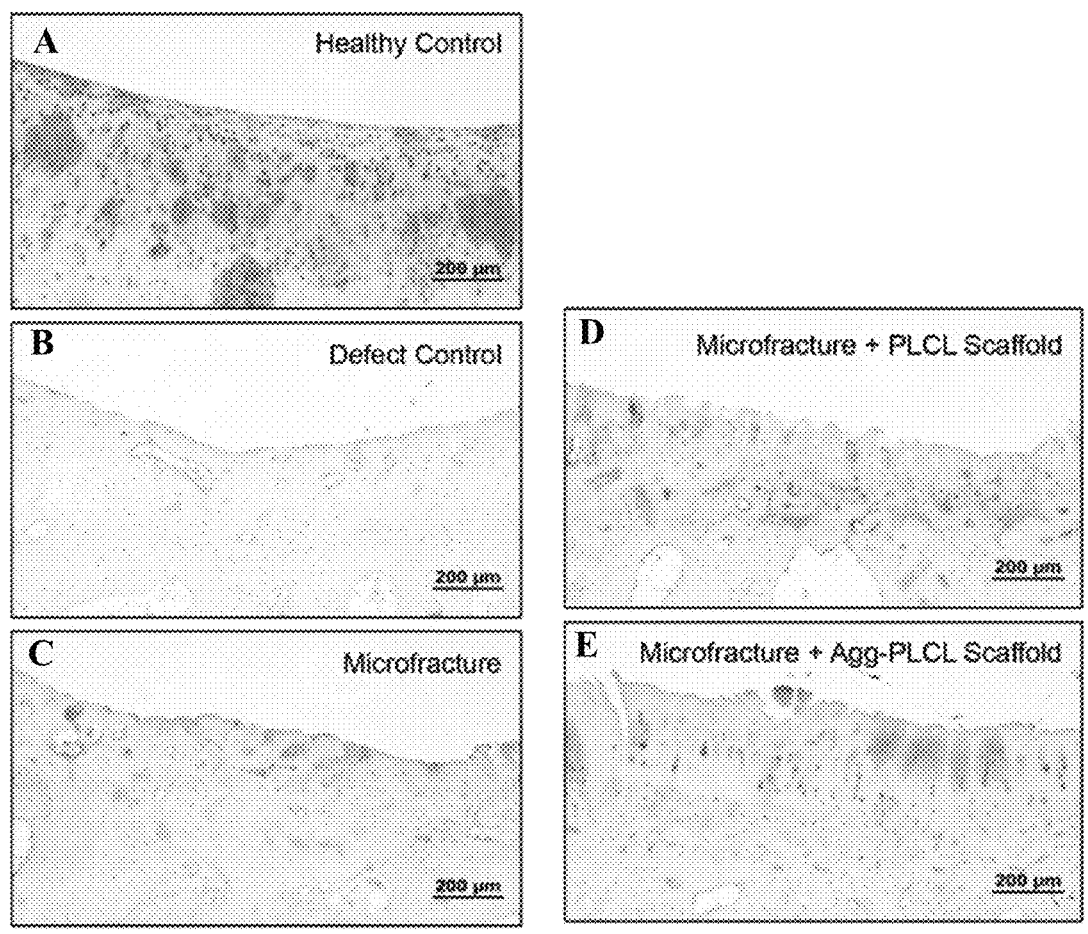
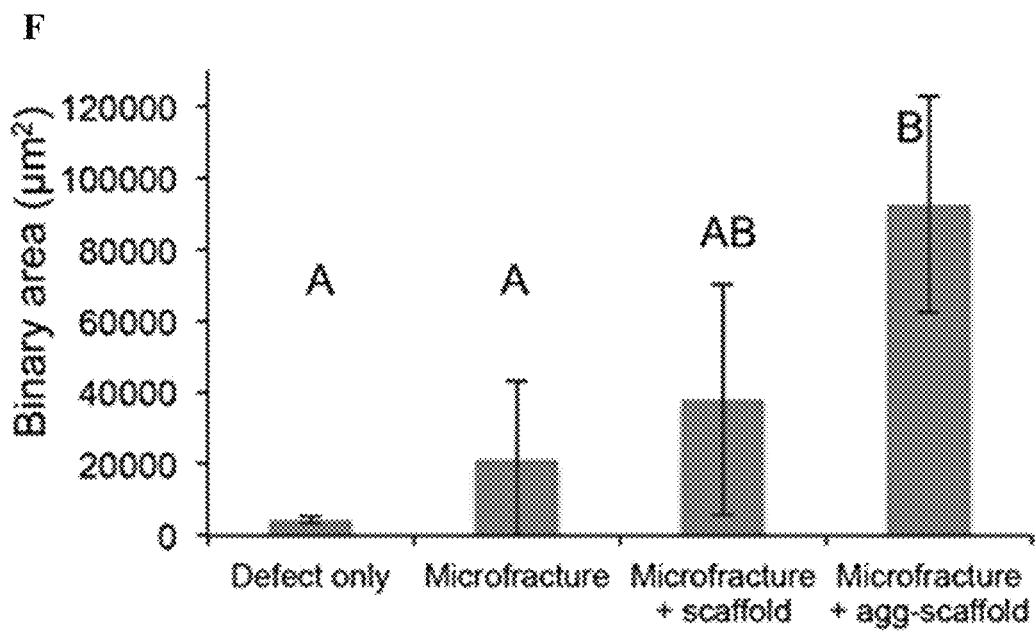

Figure 12
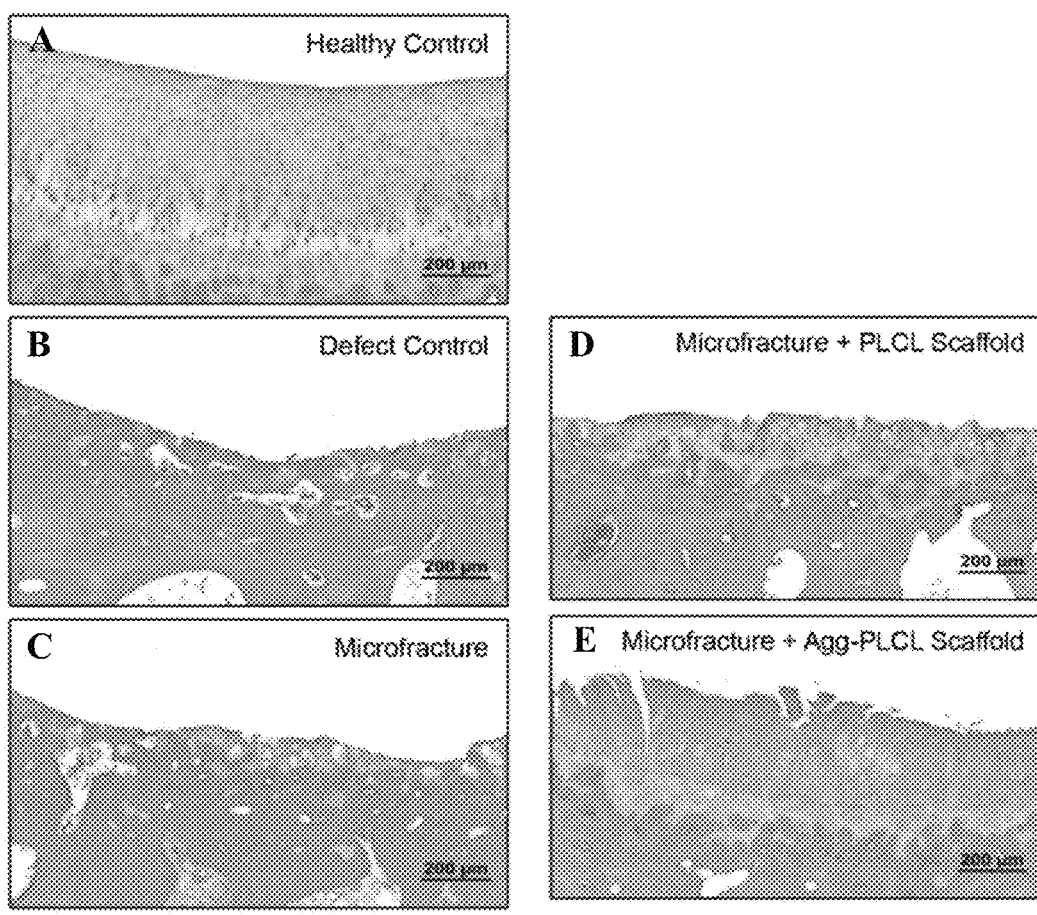
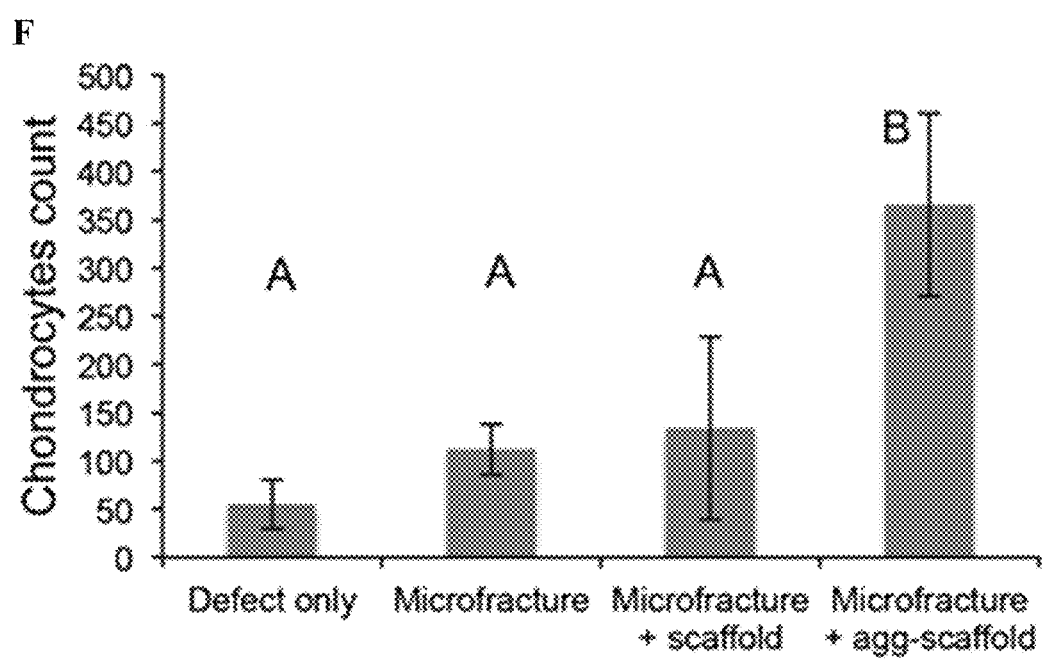

ACELLULAR BIOACTIVE SCAFFOLD DEVICE AND METHODS OF FABRICATION AND TREATMENT RELATING THERETO

CROSS-REFERENCE TO RELATED APPLICATIONS

This application is based on U.S. Provisional Patent Application Ser. No. 62/792,722, entitled "Acellular Bioactive Polymeric Scaffold to Enhance Microfracture," filed Jan. 15, 2019, and U.S. Provisional Patent Application Ser. No. 62/828,303, entitled "System, Device and Method for Cell Separation During Centrifugation," filed Apr. 2, 2019, which applications are incorporated herein by reference in their entireties and to which priority is claimed.

STATEMENT REGARDING FEDERALLY SPONSORED RESEARCH OR DEVELOPMENT

This invention was made with government support under CBET1264517 and CBET1604742 awarded by the National Science Foundation and under P41 EB023833 awarded by the National Institutes of Health. The government has certain rights in the invention.

FIELD OF THE INVENTION

The present disclosure relates to an implantable acellular scaffold device, and in particular an acellular PLCL scaffold device functionalized with aggrecan, methods of fabricating the scaffold device, and methods of treating a cartilage defect utilizing the scaffold device.

BACKGROUND OF THE INVENTION

In the US alone, the cartilage repair and regeneration market was $1.8 billion in 2015 (Grand View Research, May 2017). It is expected to grow at a compound annual growth rate of 5.4% during the next 10 years. Such growth is chiefly due to the increasing prevalence of musculoskeletal disorders, aging population, and rising number of accidents and related injuries. Cartilage defects are common in all age groups due to trauma and/or pathology, and are particularly prevalent in seniors with approximately 70% of the senior population experiencing cartilage degeneration at varying levels of severity. Over time, articular cartilage can deteriorate or become damaged following injury or normal wear and tear, leading to the pain many people feel as they age. As of 2016, approximately 14 million Americans experienced symptomatic knee osteoarthritis (Deshpande, B. R. et al. (2016) "*Number of Persons With Symptomatic Knee Osteoarthritis in the US: Impact of Race and Ethnicity, Age, Sex, and Obesity*," Arthritis Care Res 68(12):1743-1750), demonstrating a huge need for the development of translational clinical therapies. Unfortunately, the treatment and repair of articular cartilage defects remains challenging due to the limited endogenous regeneration of the tissue and poor integration with conventional implantations. As such, little long term success has been achieved with current treatment strategies.

Articular cartilage is the highly specialized connective tissue surrounding surfaces at joints. Its primary function is to protect these surfaces by providing smooth, low friction contact and enabling smooth load transfers at the joints. Articular cartilage is structurally complex and difficult to mimic, despite the fact that it is innervated and lacks blood vessels, nerves, and lymphatics. Articular cartilage is composed exclusively of chondrocytes embedded within a dense extracellular matrix (ECM) composed of water, collagen (primarily type II), hyaluronic acid, and proteoglycans (Cohen, N. et al. (1998) "*Composition and dynamics of articular cartilage: Structure, function, and maintaining healthy state*," J Ortho & Sports Phys Ther 28(4):203-215). It includes a banded structure composed of three zones: superficial, transitional, and deep, corresponding to the cartilage depth. The distinct alignment of cells and collagen fibers in each of these zones provides specific support against mechanical loadings.

As the ECM constitutes more than 90% of the dry weight of articular cartilage, it is important to understand and restore the ECM function in cartilage tissue engineering. The ECM of cartilage can be divided into 3 regions: pericellular, territorial, and interterritorial (based on its composition and properties that it lends to cartilage). The pericellular matrix comprises the thin layer surrounding the chondrocytes. It is composed of mainly proteoglycans as well as other proteins, and is responsible for transducing signals to the cell when the cartilage undergoes load bearing. It is believed that the territorial matrix contributes to protecting chondrocytes from mechanical stresses and strains caused, providing strength to the cartilage to endure loads. The interterritorial region composes the largest percentage of the ECM and thus provides most of its mechanical properties. Large collagen fibers with the highest concentration of proteoglycans are randomly oriented throughout this region in order to provide compressive strength.

Proteoglycans play an important role in the ECM as the overall negative charge retains water molecules. The resulting swelling pressure allows the tissue to resist compressive force (Yanagishita, M. (1993) "*Function of proteoglycans in the extracellular-matrix*," Acta Pathologica Japonica 43(6): 283-293). The most abundant proteoglycan within the ECM of articular cartilage is aggrecan, structured as a core protein decorated with several types of sulfated glycosaminoglycans (GAGs), including chondroitin sulfate and keratan sulfate. Multiple aggrecan monomers self-assemble into large molecules through covalent bonds with hyaluronic acid, forming large biologically active aggregated proteoglycans which carry a negative charge, resulting in significant amounts of water being retained by the tissue (Kiani, C. et al. (2002) "*Structure and function of aggrecan*," Cell Res 12(1):19-32; Guo, T. et al., "*Engineering Niches for Cartilage Tissue Regeneration*," in: A. Vishwakarma, J. Karp (Eds.), Biology and Engineering of Stem Cell Niches, Elsevier, 2017).

Microfracture and autologous chondrocyte implantation (ACI) are currently the most common surgical methods for treating cartilage defects. Microfracture surgery entails drilling small holes into the subchondral bone underlying a cartilage defect in order to trigger the release of native mesenchymal stem cells (MSCs) from the bone marrow. The MSCs differentiate into chondrocytes to regenerate articular cartilage tissue (Hurst, J. et al. (2010) "*Rehabilitation Following Microfracture for Chondral Injury in the Knee*," Clinics in Sports Medicine 29(2):257). However, the post-surgical microenvironment created by conventional techniques fails to orient and guide the MSCs to the defect site properly, resulting in comparatively weak fibrous tissue be created that does not possess the desired and necessary mechanical properties as compared to native cartilage (Steadman, J. R. et al. (2003) "*Outcomes of microfracture for traumatic chondral defects of the knee: average 11-year follow-up*," Arthroscopy 19(5):477-84; Steinwachs, M. R. et al. (2008) "*Marrow stimulation techniques*," Injury 39:26-31).

ACI is a two stage operative procedure sometimes used to treat larger defects. A small piece of articular cartilage is removed from a patient's knee in a first operation. The cartilage biopsy is then enzymatically treated in order to isolate and harvest chondrocytes. The harvested chondrocyte population is expanded over approximately 6 to 8 weeks, and then injected under an implanted patch in the patient in a second operation. ACI is typically recommended only for defects larger than two square centimeters and requires extensive recovery time after the surgeries. Additionally, it remains difficult to harvest and successfully cultivate a large enough chondrocyte population to transplant due to the low proliferation rate and differentiation potential during in vitro culture (Jones, D. & Peterson, L. (2006) "*Autologous chondrocyte implantation*," Journal of Bone and Joint Surgery-American, 88A(11):2502-2520; Hinckel, B. B. & Gomoll, A. H. (2017) "*Autologous Chondrocytes and Next-Generation Matrix-Based Autologous Chondrocyte Implantation*," Clin Sports Med 36(3):525-548). The relatively recent FDA-approved product Matrix-Induced Autologous Chondrocyte Implantation (MACI) provides for culturing of the chondrocytes in a membrane or matrix and then implanting the chondrocyte-seeded matrix. MACI showed some improved results as compared to traditional ACI (Kon, E. et al. (2012) "*ACI and MACI*," J Knee Surgery 25(1):17-22); however, MACI displayed the same drawbacks as ACI, including the requirement for the dual-surgery procedures and less abundant cell source.

Microfracture alone has been shown to be more cost-effective than ACI when comparing clinical scores (e.g., hospital costs, physical therapy, etc.) (Aae, T. F. et al. (2018) "*Microfracture is more cost-effective than autologous chondrocyte implantation: a review of level 1 and level 2 studies with 5 year follow-up*," Knee Surgery, Sport. Traumatol. Arthrosc. doi:10.1007/s00167-017-4802-5). As such, microfracture has been extensively used and has dominated the intrinsic repair stimulus segment despite its limitations. For example, an analysis of U.S. commercial insurance databases indicates that among patients undergoing microfracture surgery for cartilage repair, the average two-year reoperation rate is 15% (Frank, R. M. et al. (2018) "*Reoperation Rates After Cartilage Restoration Procedures in the Knee: Analysis of a Large US Commercial Database*," Am. J. Orthop 47(6)). Moreover, patients undergoing microfracture were more likely to experience an ultimate conversion to arthroplasty as compared to ACI and other conventional techniques.

Current treatment techniques result in newly formed tissue that is mechanically weakened by unexpected biological changes over time, leading to a loss of tissue function. Although autografts and allografts have been used to treat critical cartilage defects with limited success, there is no satisfactory treatment remedy for severe critical cartilage injuries. To improve upon the microfracture technique, some researchers have attempted to utilize the procedure with the use of biocompatible materials as defect implants. Investigators have shown that the application of hyaluronic acid (HA) after microfracture promoted thicker, hyaline-like cartilage compared to controls in a rabbit model (Leela, S. K. et al. (2008) "*Articular cartilage regeneration with microfracture and hyaluronic acid*," Biotechnol. Lett. 30:435-9). A recent clinical trial using injected HA as postoperative treatment also indicated some improved performance compared to microfracture alone (Doral, M. N. et al. (2012) "*Treatment of osteochondral lesions of the talus with microfracture technique and postoperative hyaluronan injection*," Knee Surgery, Sport. Traumatol. Arthrosc. 20:1398-1403). In another study, chitosan-glycerol phosphate/blood clots were implanted after microfracture, which was reported as showing an increased filling of the defect (Hoemann, C. D. et al. (2005) "*Chitosan-glycerol phosphate/blood implants improve hyaline cartilage repair in ovine microfracture defects*," J. Bone Jt. Surg.—Ser. A 87:2671-2686).

Other tissue engineering strategies have attempted to pursue the regeneration of biomimetic cartilage tissue utilizing various concentrations of collagen type II in a construct (Guo, T. et al. (2017) "*Three-Dimensional Printing Articular Cartilage: Recapitulating the Complexity of Native Tissue*," Tissue Engineering Part B—Reviews 23(3): 225-236). Others have attempted to isolate chondrocytes from the different cartilage zones and seed them onto scaffolds in an effort to replicate the banded structure in native articular cartilage (Mainil-Varlet, P. et al. (2001) "*Articular cartilage repair using a tissue-engineered cartilage-like implant: an animal study*," Osteoarthritis and Cartilage 9:S6-S15). In addition to the limited biological complexity involved, extensive preparation and characterization are required for these approaches.

Attempts to provide constructs for guiding cartilage repair have also been proposed, and several commercial products are currently available using specific biomaterials, including: polylactin, polydiaxanon and fibrin (BioTissue Technologies, Freiburg, Germany); collagen type I matrix (Arthro Kinetics Biotechnology, Krems, Austria); fibrin, hyaluronic acid (Histogenics Corp., Waltham, Mass.); agarose, alginate hydrogel (Tissue Bank of France, Lyon, France); bovine collagen (Histogenics Corp. Waltham, Mass.); and bovine collagen, chondroitin sulphate (Tetec Tissue Engineering Technologies AG, Reutlingen, Germany). However, constructs formed from such materials exhibit much weaker mechanical properties as compared to native cartilage, as noted above. Moreover, such conventional constructs incorporate the use of autologous cells, which may minimize the risk for immune rejection but involve a relatively lengthy surgical procedure (e.g., cell harvesting, expansion, encapsulation in biomaterial) as well as a relatively short product shelf life. Further, conventional strategies fail to provide for the regeneration of the cartilage zonal composition, as discussed in further detail below. Such conventional constructs and/or products have therefore not been successful in meeting the needs of clinicians and patients.

Accordingly, there is a need for an implantable scaffold device that solves one or more of the limitations associated with conventional cartilage repair strategies, and/or that enhances conventional cartilage repair strategies such as microfracture surgery.

SUMMARY OF THE DISCLOSURE

The present disclosure relates to an implantable acellular scaffold device that facilitates cellular growth. The scaffold is preferably fabricated using three-dimensional (3D) printing methods, and thus may be readily formed in minutes and in a selected geometric configuration suitable for the intended application. 3D printing and bioprinting enables spatiotemporal layer-by-layer fabrication of highly complex tissues such as cartilage structure. The scaffold is preferably fabricated from a composition comprising poly(L-lactide-co-caprolactone) (PLCL) and poly(lactic-co-glycolic acid) (PLGA).

An advantageous feature of the disclosed scaffold devices is the presence of an internal architecture that guides the ingrowth and differentiation of cells, e.g. such as cells released from the bone marrow via microfracture surgery. The disclosed techniques leverage the intrinsic regenerative ability of the human body and provide a physiological template for tissue repair. This paradigm can be applied to a range of applications where a clear source of endogenous stem cells is present, e.g. such as in the knee. The particular configuration of the disclosed implant may be readily modified to match other orthopedic tissue defects (e.g., shape, mechanical properties, composition, etc.) due in part to the use of 3D printing and established biomaterials for fabrication.

In some embodiments, an acellular scaffold that mimics the structure of native cartilage is used to facilitate the growth of cartilage in combination with microfracture surgery. The scaffold is preferably functionalized with aggrecan in order to provide binding sites for MSCs released from the microfracture procedure, thereby improving therapeutic functionality by increasing the repair mechanisms in microfracture. Aggrecan supports the cellular fraction of bone marrow released from microfracture. The disclosed scaffold guides MSCs and growth factors released from the bone marrow to the defect site(s), thereby initiating and/or strengthening the cartilage regeneration process. The biofunctionalized 3D-printed acellular scaffolds may thus be readily utilized in combination with traditional microfracture in order to improve the quality of cartilage regeneration in a cost and labor effective way.

In accordance with disclosed methods, a substantial improvement of regenerated cartilage tissue quality and joint function was demonstrated in animal models. Optical coherence tomography (OCT) revealed doubled thickness of the regenerated cartilage tissue in the group treated with the disclosed aggrecan-functionalized scaffold as compared to the group treated with standard microfracture alone. Haematoxylin and eosin (H & E) staining showed 366±95 chondrocytes present in the unit area of cartilage layer with the support of the disclosed bioactive scaffold implants, while the group treated with microfracture alone showed only 112±26 chondrocytes. In addition, the expression of type II collagen appeared almost 10 times higher in the group treated with the disclosed scaffold as compared to the group treated with microfracture alone, thus demonstrating a significant improvement in cartilage formation when microfracture is combined with the disclosed scaffolds as compared to microfracture alone. The therapeutic effects of the disclosed techniques were also evaluated at the joint function level. Mobility of animal models was evaluated using a modified Basso, Beattie and Bresnahan (BBB) scale. While the defect control group showed no movement improvement over the course of study, all other experimental groups showed a trend of increasing scores (and thus mobility improvement) over time.

In accordance with disclosed embodiments, the present disclosure relates to an implantable device comprising an acellular polymeric scaffold functionalized with aggrecan. In some embodiments, the scaffold is fabricated from a composition comprising poly(L-lactide-co-caprolactone) (PLCL). In some embodiments, the composition further comprises amine end capped poly(lactic-co-glycolic acid) (amine-PLGA) as a reactive portion to bind the aggrecan. The scaffold is preferably fabricated via three-dimensional (3D) printing, e.g., via material extrusion 3D printing.

In some embodiments, the scaffold comprises a first layer having a first fiber pattern, and a second layer having a second fiber pattern different from the first fiber pattern. In some implementations, the first fiber pattern comprises a plurality of spaced parallel fibers, and the second fiber pattern comprises a plurality of spaced parallel fibers. In some embodiments, the plurality of spaced parallel fibers of the first fiber pattern are offset in plan view from the plurality of spaced parallel fibers of the second fiber pattern. The second fiber pattern may comprise a generally crosshatch pattern in plan view. In some embodiments, the first layer has a first thickness, and the second layer has a second thickness at least about twice the first thickness. In some embodiments, the scaffold comprises a third layer having a third fiber pattern different from the first and second fiber patterns. In some implementations, the third fiber pattern comprises a plurality of spaced parallel fibers, wherein the plurality of spaced parallel fibers of the third fiber pattern are generally perpendicular in plan view from the plurality of spaced parallel fibers of the first fiber pattern.

The present disclosure also relates to a method of treating a cartilage defect in a subject, comprising the steps of: creating an opening(s) in a subchondral bone in the subject underlying the cartilage defect and into bone marrow thereof to permit release of mesenchymal stem cells (MSCs) from the bone marrow; and applying an acellular polymeric scaffold functionalized with aggrecan onto the cartilage defect, thereby guiding the MSCs released from the bone marrow through the openings and into the scaffold. In some embodiments, the opening(s) are created via a microfracture procedure.

The present disclosure also relates to a well plate lid comprising a base and a plurality of wells extending outwardly therefrom. The plurality of wells are receivable in correspondingly configured wells of a cell-culture plate. In some embodiments, the plurality of wells of the lid are releasably securable in the wells of the cell-culture plate via interference fit. In some embodiments, the lid is formed from and/or comprises an acrylate-based resin. In some embodiments, the lid is fabricated via three-dimensional (3D) printing, e.g. material extrusion 3D printing.

In some embodiments, at least one well(s) of the lid comprises a retaining member extending outwardly from an interior sidewall of the well(s). In some embodiments, the retaining member extends between opposing surfaces of the interior sidewall of the well(s). For example, the retaining member may have a generally cross-shaped configuration in plan view. However, it should be understood that the retaining member may have other configurations. In addition, the specific configuration of the well(s) of the lid and corresponding well plate may vary (e.g., cylindrical, square, etc.) as desired for a particular application. In some implementations, the retaining member is disposed intermediate an interior base and an upper edge of the sidewall of the well(s) of the lid. In some implementations, the retaining member is configured to retain a scaffold construct in a selected position within said well.

The present disclosure also relates to a centrifugation system comprising the well plate lid as disclosed herein, and a correspondingly configured cell-culture well plate. The centrifugation system may also include a centrifuge device operably associated with the lid and well plate.

BRIEF DESCRIPTION OF THE DRAWINGS

The patent or application file contains at least one drawing/photograph executed in color. Copies of this patent or patent application publication with color drawings/photographs will be provided by the Office upon request and payment of the necessary fee.

FIG. 11 shows an histological examination of regenerated cartilage tissue using Alcian blue staining. Alcian Blue staining showing the glycosaminoglycan (GAG) production in the different groups is shown: Healthy control group (Panel A); Defect control group (Panel B); Microfracture group (Panel C); Microfracture+PLCL scaffold group (Panel D); and Microfracture+Aggrecan-PLCL scaffold group (Panel E). Cell nuclei were stained purple and surrounding GAGs were stained blue. The GAG expression level was quantified by binary area (Panel F). Compared to defect control, microfracture and PLCL showed increased production of GAGs from the histology staining. The addition of aggrecan further improved the quality of regenerated tissue, with visible lined chondrocytes surrounded by GAGs. Data is shown as mean±standard deviation. ANOVA was performed to compare the statistical significance among groups. Means that do not share the same letter are significantly different.

FIG. 12 shows an histological examination of regenerated cartilage tissue using H & E staining in the different groups: Healthy control group (Panel A); Defect control group (Panel B); Microfracture group (Panel C); Microfracture+PLCL scaffold group (Panel D); and Microfracture+Aggrecan-PLCL scaffold group (Panel E). H & E staining showing newly regenerated cartilage tissue. Cell nuclei were stained purple and the background tissue was stained pink. The cartilage layer presents a lighter pink than the bone tissue. The number of chondrocytes was calculated and compared among groups (Panel F). The chondrocyte number in the aggrecan functionalized group was significantly higher than other experimental groups. N=3. Data is shown as mean±standard deviation. ANOVA was performed to compare the significance among groups. Means that do not share the same letter are significantly different.

DETAILED DESCRIPTION OF EMBODIMENTS

Figure 1:
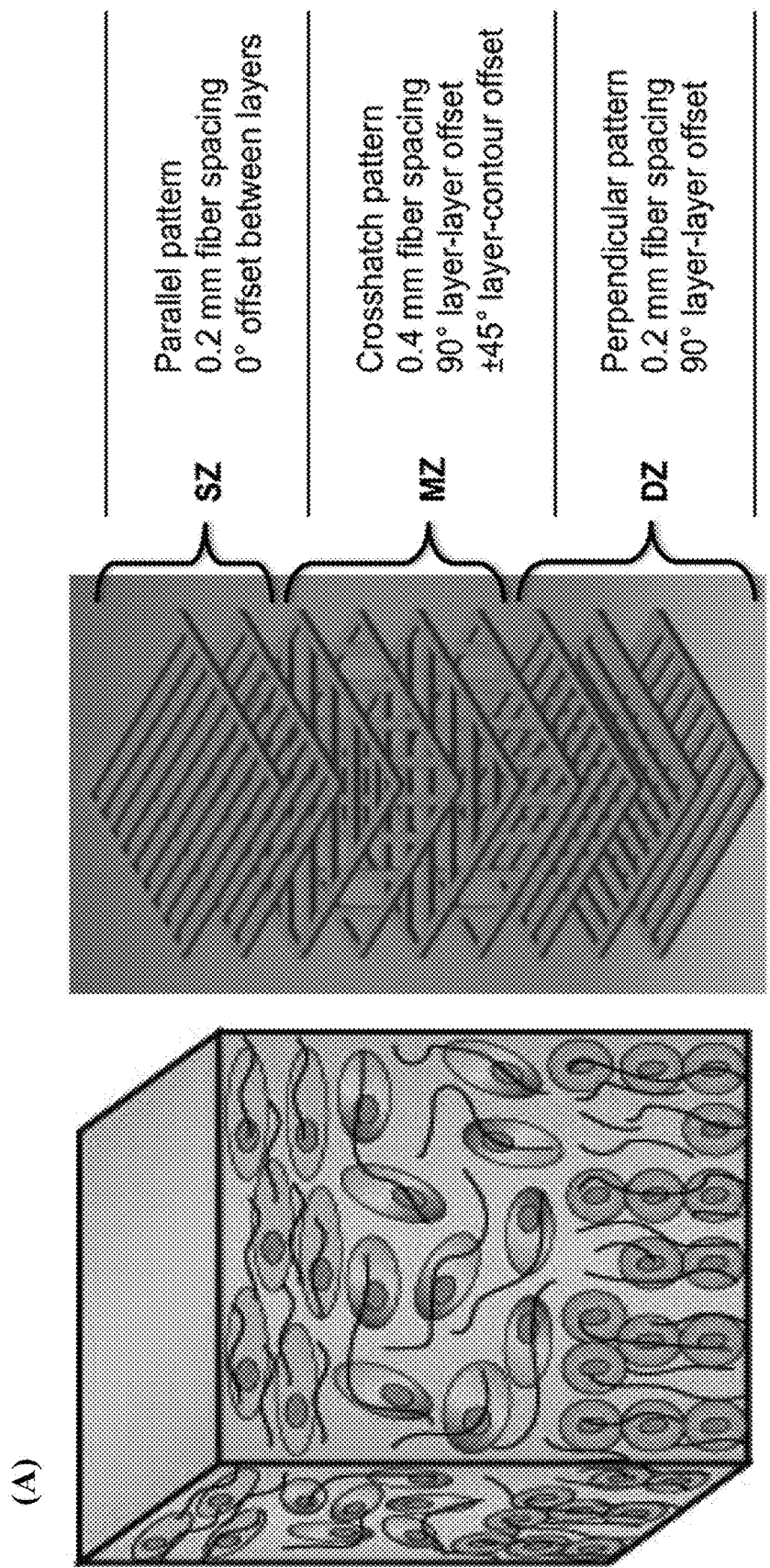
FIG. 1 illustrates cartilage structure and an exemplary implant design including three zonal patterns. Panel A shows, from left to right: a schematic illustration of cartilage zonal structure; an exploded view of CAD model implant zonal layers; and descriptions of zonal layer patterns. Panel B shows, from left to right for each zonal pattern: description of zonal layer pattern; CAD model implant layer pattern; image of printed implant layer patterns; top view of CAD implant layer pattern; and side view of CAD implant layer pattern. The top and side views show the designed pore patterns to guide multizonal cartilage formation from resident stem cells (arrows).
Figure 1:
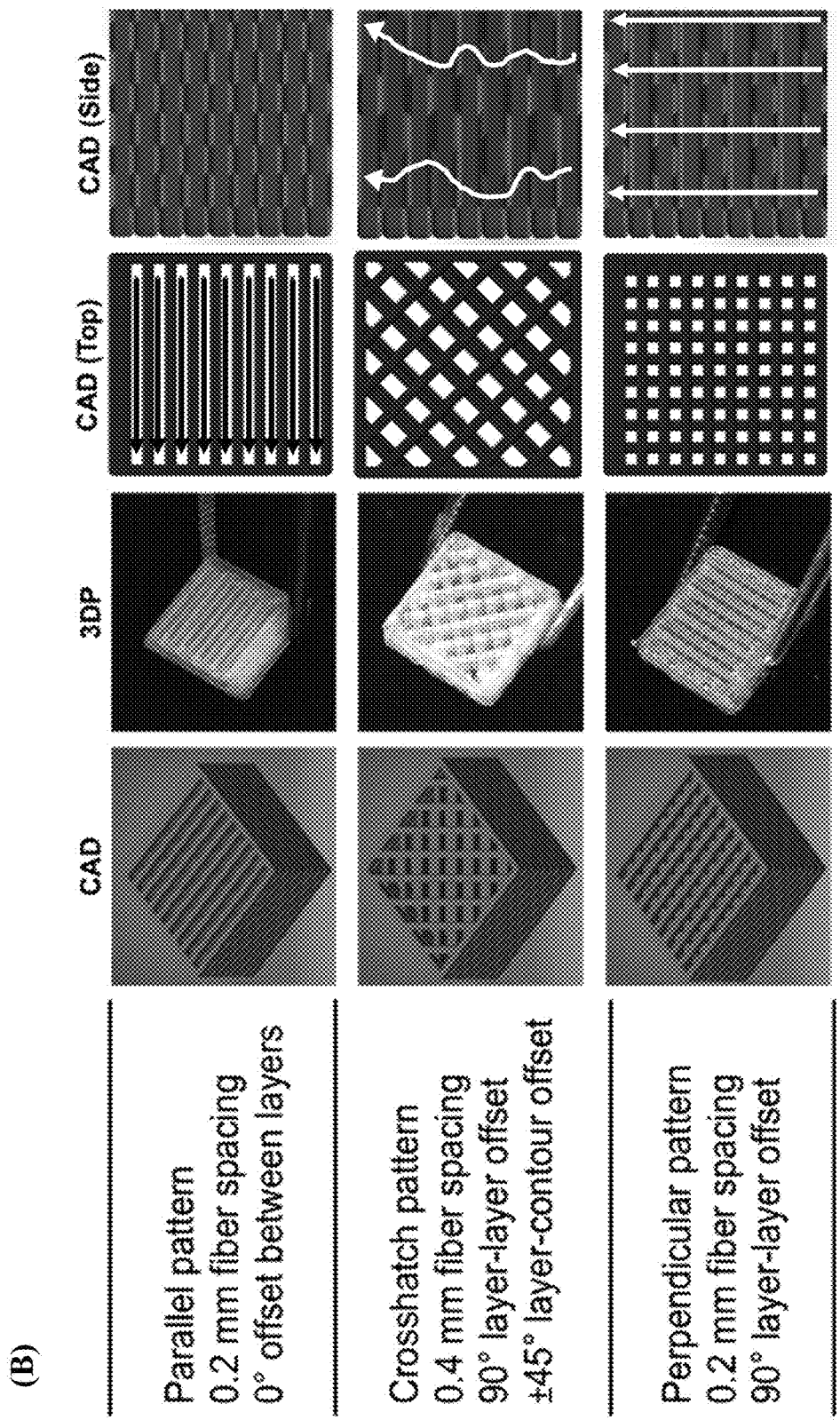

Biologically active, acellular scaffolds are an attractive alternative to cell-laden constructs given the advantages in manufacturing and preservation as a clinical product. 3D printing technology has been used to manufacture scaffolds to provide a favored cellular environment, and allows for custom shapes and consistent quality (Mironov, V. et al. (2003) "*Organ printing: computer-aided jet-based 3D tissue engineering,*" Trends Biotechnol 21(4):157-61). To further enhance the cartilage healing process, the present disclosure provides for a bioactive acellular, 3D-printed poly(L-lactide-co-caprolactone) (PLCL) scaffold implant, which is preferably surface modified with aggrecan.

In accordance with the present disclosure, a scaffold implant is specifically designed to guide the ingrowth and differentiation of host MSCs, thus providing a template for proper cartilage regeneration. Disclosed implants are engineered to fully exploit the regenerative potential of host stem cells and, unlike previous approaches, enable the recapitulation of the cartilage zonal architecture that has been shown to impact cartilage physiology and patient functional outcomes.

In accordance with disclosed embodiments, a bioactive acellular scaffold implant is provided that is suitable for use in combination with microfracture surgery in order to further enhance cartilage regeneration. The disclosed treatment methods substantially improved type II cartilage regeneration (10×), tissue thickness (1.9×), GAG content (4.4×), and number of chondrocytes present (3.2×), as compared to conventional microfracture techniques, and showed significantly improved cartilage repair as compared to conventional techniques. The fabrication of the disclosed surface-modified scaffold was done prior to surgery with no extensive additional surgical preparation required, and thus provides substantial benefit as compared to conventional microfracture procedures. Moreover, as compared to cell-based treatments and conventional scaffold designs, the advantages associated with the covalently modified acellular scaffolds disclosed herein demonstrated superior characteristics in treating large cartilage defects in a much more cost and labor effective manner as compared to conventional strategies.

When taking into consideration the type of polymer that should be utilized to fabricate the scaffold, the ability to withstand compressive mechanical stimuli is important. In comparison to prior scaffolds composed solely of poly(lactic acid) (PLA) and/or poly(lactic-co-glycolic acid) (PLGA), the disclosed scaffolds comprise one or more layers formed from poly(L-lactide-co-caprolactone) (PLCL). The scaffolds exhibited surprisingly superior properties, including toughness comparable to that of native cartilage (see, e.g., Athanasiou, K. A. et al. (1991) "*Interspecies comparisons of in situ intrinsic mechanical properties of distal femoral cartilage,*" J Orthop Res 9(3):330-40). Assessment of the extracellular matrix accumulation on the cell-inoculated PLCL scaffolds disclosed herein demonstrated that the PLCL material significantly enhanced chondrogenic differentiation (see, e.g., Jung, Y. et al. (2008) "*Cartilage regeneration with highly-elastic three-dimensional scaffolds prepared from biodegradable poly(L-lactide-co-epsilon-caprolactone,*" Biomaterials 29(35):4630-6).

Interestingly, the addition of aggrecan significantly lowered the compressive modulus of the wet PLCL scaffold, possibly due to the water retaining effect on plasticizing during mechanical testing. Proteoglycans are a defining factor in force-transmission, growing healthy ECM, and determining the viability of chondrocytes in cartilage. The approach disclosed herein provides for the novel use of aggrecan to strengthen the biological function of a 3D-printed scaffold for tissue regeneration. A prominent indication of aggrecan aiding the chondrocyte microenvironment was increased cell adhesion as quantified by DNA extraction (10×) and flow cytometry (13.6×) from whole bone marrow.

The presence of aggrecan increases the link protein on the cell surface and thus improves cell attachment (see Yang, B. B. et al. (1998) "*Aggrecan and link protein affect cell adhesion to culture plates and to type II collagen*," Matrix Biol 16(9):541-61). As the main proteoglycan component in native articular cartilage, the unique complex structure of aggrecan provides functionality that other molecules cannot replicate (Jin, R. et al. (2010) "*Synthesis and characterization of hyaluronic acid-poly(ethylene glycol) hydrogels via Michael addition: An injectable biomaterial for cartilage repair*," Acta Biomater 6(6): 1968-77; Nettles, D. L. et al. (2004) "*Photocrosslinkable hyaluronan as a scaffold for articular cartilage repair*," Ann Biomed Eng 32(3):391-7). In particular, aggrecan provides binding sites to better recruit stem cells and growth factors to aggregate on the scaffold surface and increase cell attachment. Its function of trapping water in the cartilage microenvironment also enhances the physiological environment for the stem cells released from microfracture.

Thus, in accordance with embodiments of the present disclosure, the scaffold surface is preferably modified with aggrecan. Scaffolds were seeded with bone marrow and the attached cell population analyzed using a customized centrifugation assay. After in vitro evaluation, scaffold functionality was evaluated in a lapine model with microfracture, in comparison with the non-functionalized scaffold and the standard procedure. Animal movement ability and regenerated tissue quality were also assessed, as discussed in further detail below.

In a centrifugation assay, an established force was applied to separate the adhered and non-adhered cells to achieve a precise quantification of the cell population (Ferlin, K. M. et al. "*Separation of Mesenchymal Stem Cells Through a Strategic Centrifugation Protocol*," Tissue Engineering Part C-Methods 22(4):348-359). The present disclosure is also directed to a centrifugation system including a specialized lid for the well plate. Fabrication processes have been developed to create microenvironments to control cell attachment and organization on a 3D scaffold. Different scaffolds were fabricated based on the applications, and then cells were seeded on top of the scaffolds. To evaluate the cell function, after certain time the cells need to be isolated from the scaffolds and processed for further analysis. It is important to ensure the complete isolation of cells for different groups in order to achieve precise and reliable results. In prior techniques, the separation of the adhered and non-adhered cells was simply done by trypsin and buffer washes, which is labor intensive particularly when handling large amounts of sample. Moreover, a force must be applied to demonstrate the different adhesion and adsorption. Conventional techniques and devices fail to allow for batch processing of adhered and suspended cell separation from 3D scaffolds.

The present disclosure therefore provides for a novel centrifugation system and method designed for the separation of cells from 3D printed scaffolds, including scaffolds fabricated in accordance with disclosed embodiments. The system includes a covering or well plate "lid" specially designed to be compatible with standard well plate (e.g., including 12, 24, 48, etc. well plate) and allowing for the separation of adherent and non-adherent cell populations during centrifugation. In some embodiments, the lid includes an element to capture 3D printed scaffolds to separate three distinct cell populations.

In some embodiments, a cell population is attached to the bottom of the well plate and inserted scaffold, and grown in suspension in the media. The centrifugation system is superior to conventional techniques given it provides the ability to separate multiple samples simultaneously without risk of cross-contamination. The disclosed centrifugation system allows for easy recovery of multiple components, which are readily sterilizable and thus reusable, and the capability of separating multiple cell types based on adhesion characteristics without the need for additional fluorescent markers or chemical agents. In some implementations, the system includes surfaces functionalized with various materials to separate increasingly complex cell populations or facilitate culture directly within the system.

In some embodiments, the lid for the centrifugation system is 3D printed. The 3D printed lid is sized to fit the tissue culture well plate utilized, and designed to hold the 3D printed scaffolds in place while collecting the non-adhered bone marrow portion during centrifugation. For example, the lid may be configured to fit snugly into a standard 24 well plate. The lid may be 3D printed, e.g., using ENVISIONTEC™ Eshell 300 material. The lid is preferably designed with a slight interference fit to allow for centrifugation and separation of adherent and non-adherent populations.

In some embodiments, the system and device are sterilizable and thus reusable if desired, and capable of separating multiple cell types based on adhesion characteristics without the need for additional fluorescent markers or chemical agents. In some embodiments, the surfaces are functionalized, e.g., with plasma (e.g. oxygen, ammonia, etc.), small molecules and/or self-assembled monolayers (e.g. gold-thiol), and/or protein coating (e.g. fibronectin). The device is amenable to functionalization with other materials, as would be appreciated by one of skill in the art. Implementing additional surface functionality may be used to separate increasingly complex cell populations and/or to facilitate culture directly within the separator device.

In accordance with embodiments of the present disclosure, the lid may be fabricated from various biomaterials, e.g., such as polystyrene. Depending on the material, the lid is fabricated via 3D printing or molding techniques known in the art. The centrifugation system and device allows for efficient separation of adherent and suspension cells from various 3D constructs. With surface modification, the system may be utilized to further isolate different cell populations. One of skill in the art would appreciate that the specific dimensions and configuration of the lid may vary depending on the application. Thus, the lid may be readily manufactured with different dimensions, e.g., to fit different well plates. In addition, the lid may be fabricated (e.g., via 3D printing) to cover all or part of the wells as needed. For example, the lid may be fabricated to provide for partial coverage of the well plate (e.g., conventional 48-well plate or 24-well plate).

With aggrecan functionalization, cell attachment efficiency was significantly increased, as demonstrated by the disclosed data. Notably, the presence of aggrecan promoted cell adhesion regardless of cell type. Further, the percentage of hMSCs among all adhered cells was not affected by the aggrecan.

New Zealand White (NZW) rabbits were used as an animal model to further evaluate scaffold biofunctionality. NZW rabbits are well-established for use in orthopedic surgery models because the condyle of mature rabbits is large enough to incorporate scaffold treatment with feasible surgical procedures. The thickness of the cartilage layer in rabbits is also enough to prevent the potential intrinsic repair compared to mouse or rat model (Chu, C. R. et al. (2010) "*Animal models for cartilage regeneration and repair,*" Tissue Eng Part B Rev 16(1):105-15). The cartilage regeneration process varies by gender as sex hormones play a role in regulating chondrocyte function and collagen production. Specifically, female rabbits are associated with higher incidences of osteoarthritis (Garstang, S. V. & Stitik, T. P. (2006) "*Osteoarthritis: epidemiology, risk factors, and pathophysiology,*" Am J Phys Med Rehabil 85(11 Suppl):S2-14). Therefore, female rabbits were used as the model for the cartilage repair studies in order to provide for consistent cartilage physiology properties and a model associated with the disease prevalence.

Although successful, the random cell differentiation induced by microfracture often leads to the formation of fibrocartilage, which is weaker than native articular cartilage and therefore results in the loss of desired tissue function (see Steadman, J. et al. (2001) "*Microfracture: Surgical technique and rehabilitation to treat chondral defects,*" Clinical Orthopaedics and Related Research 391:S362-5369; see also Mithoefer, K. et al. (2005) "*The microfracture technique for the treatment of articular cartilage lesions in the knee—A prospective cohort study,*" Journal of Bone and Joint Surgery-American Volume 87A(9):1911-1920; and Bae, D. et al. (2006) "*Cartilage healing after microfracture in osteoarthritic knees,*" Arthroscopy—the Journal of Arthroscopic and Related Surgery 22(4):367-374). To overcome the lack of chemical cues in microfracture surgery for the released cellular component, an aggrecan-functionalized acellular scaffold was incorporated into the defect area in accordance with disclosed methodologies.

Cell based treatments require an extra surgery to source autologous cells as well as additional time for in vitro maintenance to expand the autologous or allogenic cells (Xu, X. et al. (2017) "*In vivo repair of full-thickness cartilage defect with human iPSC-derived mesenchymal progenitor cells in a rabbit model,*" Experimental and Therapeutic Medicine 14(1):239-245). In contrast, the acellular scaffolds disclosed herein may be combined with microfracture in a single surgery with little additional preparation time, substantially improving microfracture's potential for clinical translation over the use of cell-based approaches.

Some minor surgical challenges were encountered using the small animal (lapine) model. During the implantation procedure into the rabbit model, the scaffolds were fixed in place using fibrin glue. Although most of the scaffolds were degraded after 8 weeks, some minor debris was found outside the defect area. Due to the limited soft tissue in the trochlear groove after creating the critical defect, suturing the scaffold in place was not feasible. However, it is believed that this issue would be readily remedied and/or eliminated with a larger animal model and/or by incorporating a more effective biocompatible glue, which would also improve the integration of the local tissue after implantation (Drobnic, M. et al. (2006) "*Comparison of four techniques for the fixation of a collagen scaffold in the human cadaveric knee,*" Osteoarthritis Cartilage 14(4):337-44).

According to previous studies, the tissue regenerated by microfracture matures after 8 weeks (Frisbie, D. et al. (2006) "*Effects of calcified cartilage on healing of chondral defects treated with microfracture in horses,*" American Journal of Sports Medicine 34(11): 1824-1831). Therefore, the knee joints were harvested and evaluated 8 weeks post operation. Clinically, cartilage thickness is an important factor for determining the progression of osteoarthritis. Cartilage thickness was therefore measured to evaluate the regeneration potential of the different treatments. Optical coherence tomography (OCT) presents advantages over ultrasound including higher resolution, and has been used as a non-invasive method to assess tissue qualitatively and quantitatively, including rabbit cartilage (Rogowska, J. et al. (2003) "*Cartilage thickness measurements from optical coherence tomography,*" J Optical Society of America a-Optics Image Science and Vision 20(2):357-367; Han, C. W. et al. (2003) "*Analysis of rabbit articular cartilage repair after chondrocyte implantation using optical coherence tomography,*" Osteoarthritis and Cartilage 11(2):111-121). OCT therefore provided an effective mechanism to evaluate the 3D structure of the regenerated tissue in addition to histology.

The BBB score was initially developed to evaluate locomotion after spinal cord injury in rats (Basso, D. et al. (1995) "*A sensitive and reliable locomotor rating-scale for open-field testing in rats,*" Journal of Neurotrauma 12(1): 1-21). The application in a rabbit model has also been reported, although a lower range of scores were applied in the study (Yoshil, S. et al. (2009) "*Functional restoration of rabbit spinal cord using collagen-filament scaffold,*" Journal of Tissue Engineering and Regenerative Medicine 3(1): 19-25). The rabbits in the present studies exhibited much higher recovery levels, so the BBB scale was adjusted to accurately assess differences in healthy and unhealthy walking patterns. The tail balance criterion specific to rats was modified to standing abilities in this application to better differentiate recovery rates among the rabbits. In general, the score each group received matched the histological performance, although more distinct differences among treatment groups could be reflected with a more tailored scale system focusing on post-orthopedic operation. Moreover, considering the challenges of the functional level of assessment, it is reasonable that such differences were not shown during the early stages of the tissue regeneration. Even though further evaluation may establish a locomotion assessment post orthopedic surgery for rabbits, it is believed that the studies disclosed herein were the first time that tissue function was investigated through movement.

Covering the microfracture area is believed to result in a more robust cartilage regeneration. The mechanism of microfracture to treat cartilage defects is based on the released MSCs from the bone marrow and cellular differentiation with the support of growth factors and cytokines from the platelets (Shapiro, F. et al. (1993) "*Cell origin and differentiation in the repair of full-thickness defects of articular cartilage,*" J Bone Joint Surg Am 75(4):532-53). The presence of the scaffolds covering the defect area following the microfracture structurally stabilized the blood clots and resulted in better integrated tissue repair and more robust cartilage regeneration (see, e.g., Erggelet, C. et al. (2009) "*Formation of cartilage repair tissue in articular cartilage defects pretreated with microfracture and covered with cell-free polymer-based implants,*" J Orthop Res 27(10): 1353-60; see also Hoemann, C. D. et al. (2007) "*Chitosan-glycerol phosphate/blood implants elicit hyaline cartilage repair integrated with porous subchondral bone in microdrilled rabbit defects,*" Osteoarthritis Cartilage 15(1): 78-89).

In the present studies, subjects treated with an unmodified PLCL scaffold showed an overall improvement compared to subjects treated with microfracture alone. From OCT 3D scanning, the addition of the PLCL scaffold led to a smoother and more homogeneous regenerated layer of cartilage. Both Alcian blue and safranin-O staining demonstrated the improved proteoglycan formation with the treatment of the bioactive scaffold as compared to conventional microfracture alone.

The evaluation of cartilage-bone interface is important to assess the overall success of the surgical procedure (Shao, X. et al. (2006) "*Repair of large articular osteochondral defects using hybrid scaffolds and bone marrow-derived mesenchymal stem cells in a rabbit model*," Tissue Eng 12(6):1539-51; Shao, X. et al. (2006) "*Evaluation of a hybrid scaffold/cell construct in repair of high-load-bearing osteochondral defects in rabbits*," Biomaterials 27(7):1071-80; Ho, S. T. et al. (2010) "*The evaluation of a biphasic osteochondral implant coupled with an electrospun membrane in a large animal model*," Tissue Eng Part A 16(4): 1123-41). In the disclosed cartilage defect model, other than the signs from the microfracture drill, no visible difference in the subchondral bone area was observed among all the groups. An important function of aggrecan, as a major proteoglycan in native cartilage, is to mediate the chondrocyte-chondrocyte and chondrocyte-matrix interactions by stabilizing the cell-substratum interactions and sustaining the bioactive molecules in serum and fluids (Kiani, C. et al. (2002) "*Structure and function of aggrecan*," Cell Res 12(1):19-32). The G1 domain of aggrecan also plays a role in chondrocyte apoptosis (Cao, L. et al. (1998) "*Expression of the G1 domain of aggrecan interferes with chondrocyte attachment and adhesion*," Matrix Biol 17(5):379-92; Cao, L. et al. (1999) "*Chondrocyte apoptosis induced by aggrecan G1 domain as a result of decreased cell adhesion*," Exp Cell Res 246(2):527-37). As such, it is believed that this phenomenon resulted in the subjects treated with aggrecan-PLCL exhibiting a significantly enhanced healing process, as shown by the increased thickness of regenerated cartilage and increased chondrocytes and GAGs presence shown in the histology. More deposition of type II collagen in the regenerated area further confirmed the quality of the newly formed tissue and the importance of incorporating aggrecan to improve the biological function of the scaffold.

The native zonal structure of cartilage tissue is also taken into consideration in studies to restore the desired tissue function (see, e.g., Guo, T. et al. (2017) "*Three-Dimensional Printing Articular Cartilage: Recapitulating the Complexity of Native Tissue*," Tissue Engineering Part B—Reviews 23(3):225-236). The thickness of cartilage tissue in the rabbits limited the possibility of implanting a multi-zonal scaffold (FIG. 1). However, the ability of a 3D printed scaffold with a biomimetic zonal structure to induce cell alignment in different regions may be readily evaluated in a larger animal model with a longer recovery time (Guo, T. et al. (2017) "*3D printing PLGA: a quantitative examination of the effects of polymer composition and printing parameters on print resolution*," Biofabrication 9(2):024101; Guo, T. et al. (2018) "*Three dimensional extrusion printing induces polymer molecule alignment and cell organization within engineered cartilage*," J Biomed Mater Res A 106(8):2190-2199).

In accordance with the present disclosure, the PLCL scaffold functionalized with aggrecan effectively guided MSCs and/or growth factors to the defect site(s) and strengthened cartilage regeneration. As demonstrated by the data, the 3D printed scaffolds with aggrecan improved cartilage regeneration ten times more than microfracture alone or in combination with a non-functionalized scaffold. Congruently, aggrecan increased cell attachment to the scaffold by ten times in comparison to a non-functionalized scaffold and thus substantially improved cartilage repair.

The disclosed acellular scaffold devices: i) are inexpensive to fabricate; ii) may be readily approved by regulatory agencies due in part to the absence of any cell component, and to the use of established biomaterials; and iii) may be readily combined with current procedures such as microfracture, providing for a quick and smooth translation from bench-to-bedside. The disclosed scaffold devices may be readily tailored for articular cartilage repair, including hyaline cartilage which is anticipated to experience the fastest growth during the next 10-year period due to high susceptibility of damage to hyaline cartilage (e.g. osteoarthritis in aging population) and the increase in sport injuries. The disclosed methods are much less invasive as compared to other surgical treatment strategies such as mosaicplasty and joint arthroplasty, and, different from osteochondral allograft transfer arthroscopic chondroplasty, the disclosed methods do not involve the use of non-self, material/cells that may cause an adverse immune response.

In addition, the combination of the disclosed scaffold devices with microfracture is expected to result in lower reoperation rate in light of the more robust cartilage repair demonstrated. Given the improved outcome, the disclosed methods are also expected to shorten the rehabilitation period post-surgery, and accordingly result in lower costs for post-operative care (e.g. physical therapy). The disclosed treatment methods entail shorter recovery periods, lower reoperation rates, and lower need for invasive surgery (e.g. arthroplasty) at reoperation as compared to standard microfracture surgery. As such, the disclosed techniques provide for a much more convenient and time-savings repair procedure for patients as well as lower healthcare costs.

Additional characteristics and features of the present disclosure will be further understood through reference to the following additional examples and discussion, which are provided by way of further illustration and are not intended to be limiting of the present disclosure.

Example 1

Scaffold Fabrication

An exemplary scaffold implant device suitable for cartilage implant was fabricated in a layer-by-layer fashion via extrusion-based 3D printing. A scaffold implant customized for a particular patient may be readily fabricated starting from a CAD model that can be either designed using commonly available software, or directly generated from imaging data routinely collected in the clinics (e.g. MRI, CAT scan, etc.). The scaffold was extruded in three different zonal layer patterns (FIG. 1, Panel A) designed to guide the growth and differentiation of resident stem cells according to the three different zones observed in native cartilage. The three layer patterns include: i) a parallel pattern, wherein tissue ingrowth occurs in a horizontal and parallel fashion as observed in the superficial zone (SZ) of articular cartilage; ii) a cross-hatch pattern, wherein the random presence of fibers and pores results in random alignment of cells and extracellular matrix (ECM) as observed in vivo in the cartilage middle zone (MZ); and iii) a perpendicular pattern, wherein fiber alignment and porosity guide cell infiltration and tissue regeneration in a vertical fashion, similar to the cartilage deep zone (DZ) (FIG. 1, Panel B). Each of these zones has an important role in cartilage function as well as in patient motor function and comfort.

During microfracture surgery, a series of holes are drilled in the subchondral bones, resulting in the release of cells and ECM from the bone marrow into the cartilage defect. While microfracture successfully promotes neo-cartilage formation, it is also associated with the undesirable formation of fibrous cartilage at articulating surfaces that does not possess the desired mechanical properties, as discussed above. In accordance with the present disclosure, the scaffold device is specifically designed to guide the ingrowth and differentiation of host stem cells, thus provide a template for proper cartilage regeneration. The scaffold was engineered to exploit the regenerative potential of host stem cells and, unlike previous approaches, enable the regeneration of the cartilage zonal architecture. The scaffold is suitable for use in combination with microfracture surgery, and thus may be seamlessly incorporated into current surgical procedures without substantial modification to such procedures and/or to pre/post-operative care.

The use of natural materials allows for high biocompatibility but low mechanical compliance of the implant with the cartilage defect. Scaffolds were fabricated from a composition comprising poly(L-lactide-co-caprolactone) (PLCL) and amine end capped poly(lactic-co-glycolic acid) (NH2-PLGA). Differently from natural hydrogels, both materials withstand mechanical stimuli and PLCL matches mechanical properties of toughness relative to native cartilage. The scaffolds therefore possess cartilage-like mechanical properties while maintaining a high level of biocompatibility.

The presence of amine end capped PLGA in the formulation allows functionalization with ECM molecules upon fabrication. Aggrecan, an ECM protein abundant in cartilage, was successfully conjugated to a PLCL scaffold using standard EDC chemistry (FIG. 3A). As demonstrated by the data, biofunctionalization of the scaffold promoted cell/ECM retention from the bone marrow and more robust cartilage repair. Furthermore, the scaffold implants are composed of biomaterials that have been used in other FDA-approved devices and no cells are present, thereby streamlining regulatory compliance. Moreover, the shelf-life of scaffold implants disclosed herein may be as little as 2-3 weeks, depending on final packaging and the biomaterial combination selected.

Scaffold Characterization and Discussion

An extensive study was performed to assess the effect of fabrication parameters (e.g., polymer molecular weight, pressure and temperature of extrusion, etc.) on the scaffold architecture, degradation, and mechanical properties (Guo, T. et al. (2017) "*3D printing PLGA: a quantitative examination of the effects of polymer composition and printing parameters on print resolution*," Biofabrication 9(2): 024101). A statistical model was built to reveal the correlation and predominant factors that determine 3D printing precision. The model showed a strong relationship between the actual and predicted precision under different combinations of printing conditions and material compositions.

Figure 2:
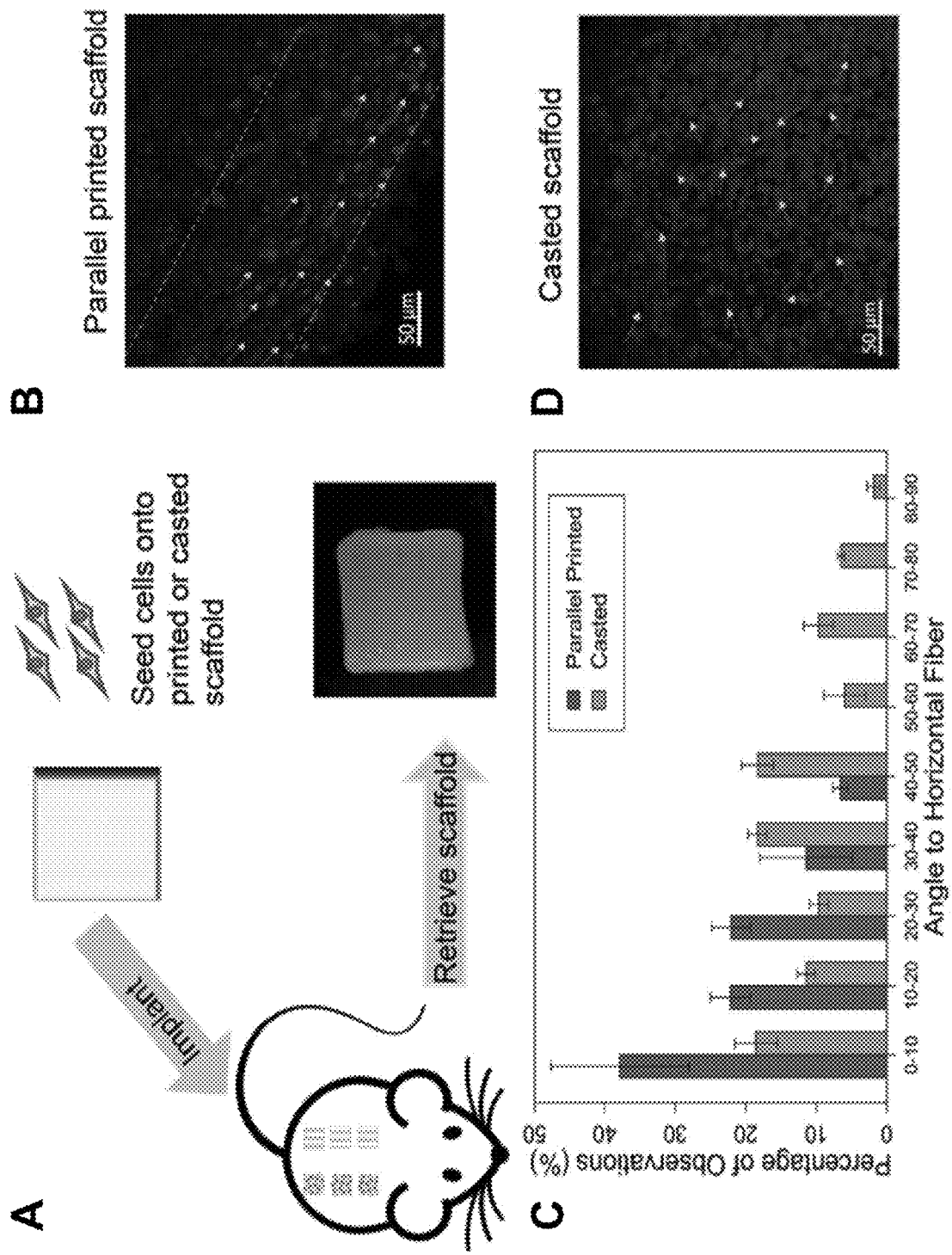
FIG. 2 shows implant pattern guide cell alignment and chondrogenic differentiation. Rat MSCs were seeded on parallel printed or casted scaffolds, and then scaffolds were implanted subcutaneously in rats (Panel A). After 7 days, cells appeared mostly aligned on the parallel patterned scaffold (Panel B), while cells were more randomly distributed on the casted scaffolds (Panel D). Panel C shows graphically quantification of cell alignment in vivo. Panel E shows graphically comparisons of chondrogenic gene expression for cells grown on scaffolds with different patterns, showing upregulation of chondrogenic markers aggrecan, collagen type 2, and PRG4 expression in the parallel pattern group. *Shows statistically significant different ($p<0.05$).
Figure 2:
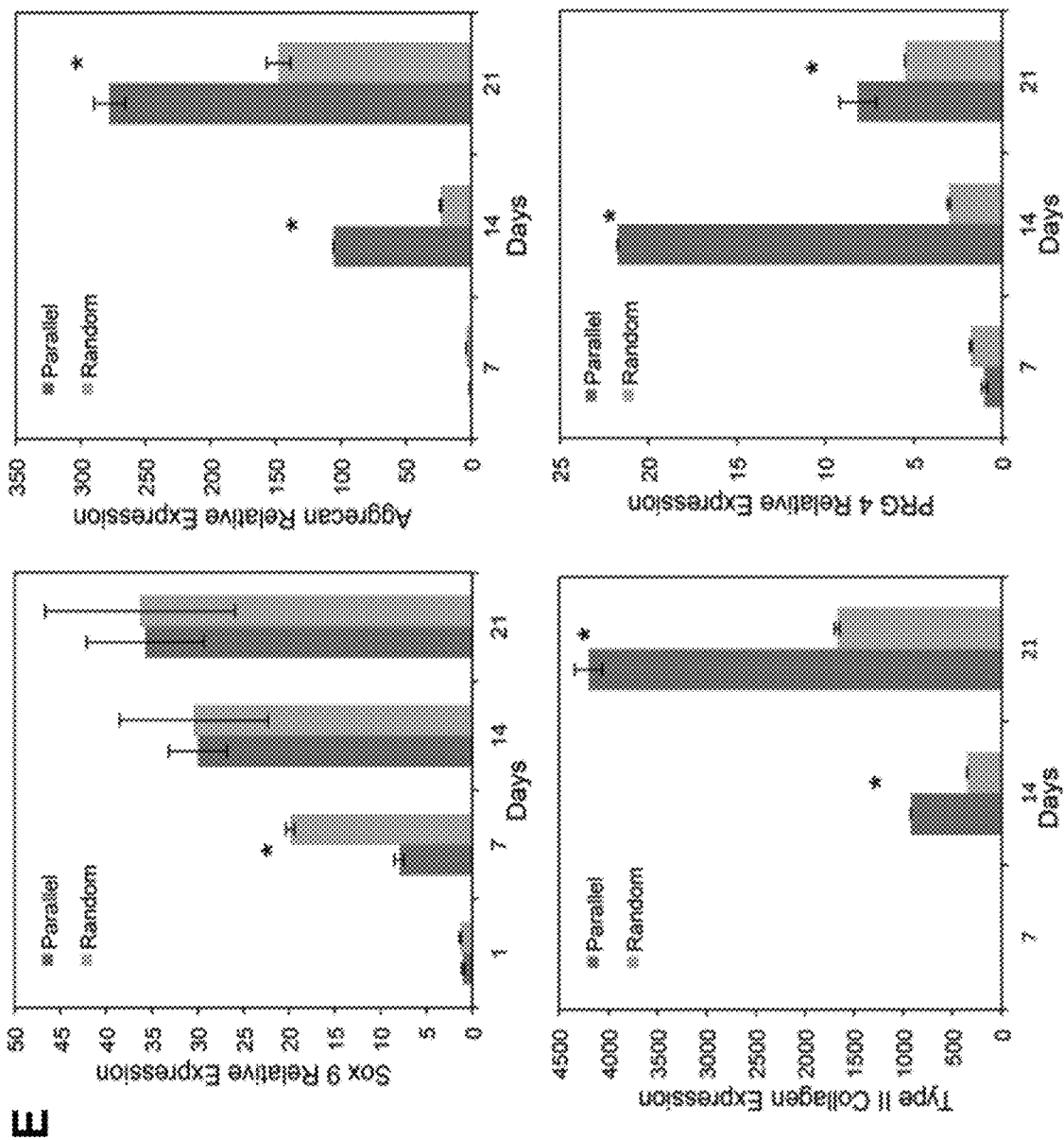

The scaffold implant was fully characterized for its ability to support cell proliferation and chondrogenic differentiation of stem cells in vitro and their ability to guide cell infiltration and alignment according to the designed pattern in vivo (FIG. 2). The recapitulation of articular cartilage zonal structure has been a great challenge in the field. In the present studies, variable cell morphology was observed among different printed patterns and printed versus casted samples. The cell shape, in turn, influenced the chondrogenic differentiation of MSCs (FIG. 2, Panel E). The achievement of zonal marker expression as a result of cell alignment is important in the development of functional cartilage tissue by engineering the cellular microenvironment.

Unlike complicated nanofabrication processes used to achieve surface patterns in many other conventional devices, the desired polymer molecule and cell alignment was readily achieved in the disclosed scaffolds via the use of extrusion 3D printing and without any additional processing. The cell orientation was maintained in vivo in a subcutaneous scaffold implant, making the disclosed approach ideal for combining with surgical procedures that release native stem cells (e.g., microfracture) for improved cartilage repair. The results on the effect of printed pattern on cell organization and differentiation demonstrated that the disclosed approach may be readily utilized to create implants with controlled cell and ECM arrangement in order to achieve optimized biological function for chondrogenesis.

Example 2

An animal study was conducted in order to evaluate the performance of microfracture surgery when combined with the disclosed scaffold implant. As demonstrated herein, the addition of an acellular PLCL scaffold device following microfracture provided effective guidance to the stem cells released from the bone marrow and resulted in substantially enhanced cartilage regeneration. The results were even more significant when using a PLCL scaffold functionalized with aggrecan, and resulted in an even higher cell/ECM retention from the bone marrow via microfracture, thicker cartilage formation, and deposition of ECM (collagen type I, glycosaminoglycans) similar to that of native cartilage.

3D-Printed Aggrecan-Functionalized Scaffold

A 3D-printed scaffold functionalized with aggrecan demonstrated a substantial improvement in the quality of regenerated cartilage tissue during microfracture as compared to conventional techniques. As the main proteoglycan component of native articular cartilage tissue, aggrecan provides binding sites to recruit stem cells and aggregates growth factors to the scaffold surface, further promoting cell attachment. The physiological environment for the MSCs released from microfracture was enhanced by the water and biological components trapped by the aggrecan, mimicking the native cartilage microenvironment.

An aim of the study was to design and verify the scaffold surface modification with aggrecan. The bone marrow and attached cell population's interaction with the scaffold were analyzed using a customized centrifugation assay described herein. After in vitro evaluation, the scaffold functionality was tested in a lapine model, comparing the standard microfracture, with non-functionalized and functionalized scaffolds. As demonstrated by the data, the combined acellular bioactive scaffold and microfracture treatment significantly improved the cartilage tissue repair outcome as compared to conventional techniques and without excessive labor or complicated procedures.

Scaffold Fabrication

Poly(L-lactide-co-caprolactone) (PLCL, PolySciTech, West Lafayette, Ind.) with a lactic acid:caprolactone ratio of 70:30 and molecular weight of 45 kD to 55 kD was combined with 15% (w/w) amine end capped poly(lactic-co-glycolic acid) (amine-PLGA, PolySciTech) to make a PLCL-amine scaffold material by grinding the polymers together to form a homogeneous mixture. Scaffolds were fabricated using the 3D BIOPLOTTER™ prototyping tool (EnvisionTEC, Gladbeck, Germany) using direct melt extrusion technique (Guo, T. et al. (2017) "*3D printing PLGA: a quantitative examination of the effects of polymer composition and printing parameters on print resolution*," Biofabrication 9(2):024101). The scaffold material composition of 15% w/w PLGA-amine and 85% PLCL was based on an estimation of amine groups needed for the reaction. The scaffold inner pattern was programmed using the provided ENVISIONTEC® software (EnvisionTEC, Inc., Dearborn, Mich.). For printing, material was loaded in the printing cartridge and melted at 155° C. for extrusion at 6.5 bar with an average speed of 4 mm/s using a 0.2 mm inner diameter stainless steel needle. Scaffolds had dimensions of 3 mm (length)×3 mm (width)×0.5 mm (height) (FIG. 3C). Particularly, in the bone marrow seeding study, scaffolds were fabricated with a disk shape and a diameter of 7 mm to maximize the covered area in the well plate.

Aggrecan Functionalization of Scaffolds Through Covalent Bonding

Aggrecan was covalently bound to the printed scaffolds via covalent bonding of EDC and sulfo-NHS (FIG. 3A). Aggrecan naturally has many free carboxyl bonds, and EDC and NHS converts carboxyl groups to reactive ester that will react to free amines. EDC acts as a linker and covalently binds the glycolic group on aggrecan molecules to the amine group on the printed PLCL scaffolds. 1-ethyl-3-[3-dimethlaminopropyl] carbodiimide (EDC, Thermo Fisher Scientific, Waltham, Mass.) and N-hydroxysulfosuccinimide (sulfo-NHS, Thermo Fisher Scientific, Waltham, Mass.) were used to link the carboxyl group on aggrecan molecules to the amine group on the printed PLCL scaffolds. PLCL-amine scaffolds were soaked in 0.1M 2-[morpholino]ethanesulfonic acid buffer (MES, Sigma-Aldrich, St. Louis, Mo.) for 15 minutes prior to aggrecan functionalization. For each scaffold, a functionalization solution was composed of 0.5 mg lyophilized bovine aggrecan (Sigma-Aldrich), 1 mL MES buffer, 1.6 mg EDC, and 4.4 mg sulfo-NHS and allowed to react for 15 minutes based on the EDC-NHS reaction manufacturer protocol. Scaffolds were placed in the functionalization solution and placed on the shaker at 50 rpm to react for 2 hours. Scaffolds were washed with phosphate-buffered saline (PBS, Sigma-Aldrich).

Nuclear Magnetic Resonance Spectroscopy

Bruker ADVANCE III 600™ nuclear magnetic resonance (Bruker Corp., Billerica, Mass.) spectrometer with BBFO gradient probe was used for the $^1$H NMR experiments. Polymer samples were dissolved in dimethyl sulfoxide-$d_6$ ($CD_3SOCD_3$). The internal solvent signal 6 ($CD_3SOCD_3$)= 2.5 ppm was used as reference. Aggrecan was dissolved in $D_2O$ at 1 mg/ml. Printed scaffold functionalized with aggrecan (PLCL-aggrecan) was dissolved in $CD_3SOCD_3$/deuterium oxide ($D_2O$) at 2:1 ratio for better solubility. Solvent suppression pulse sequence was used to suppress solvent $^1$H signal for aggrecan and PLCL-aggrecan samples to achieve the optimum sample signals. A total of 64 scans were used for $^1$H experiments, and 128 scans for solvent suppression experiments.

Compressive Mechanical Testing

Mechanical testing was performed on the printed PLCL-amine and aggrecan functionalized PLCL-amine scaffolds (N=6 for each group) using an Instron mechanical testing system (33R/4465) (Instron Engineering Corp., Norwood, Mass.). The scaffolds were wet in PBS for 24 hours before the compressive mechanical properties were evaluated. All samples were compressed by a 50N load cell at a displacement rate of 0.5 mm/min with a pre-load of approximately 0.05N until the machine protection distance was reached. For every 10 ms, compressive stress and strain were recorded and calculated based on the original cross-sectional area and height of the wet scaffold. The compressive modulus was then determined by definition, which is the slope of the linear region of the stress-strain curve before failure.

Cell Culture and Seeding

Human MSCs (hMSCs, RoosterBio, Frederick, Md.) were expanded in RoosterNourish high performance MSC media according to the manufacturer's recommendations and grew 10 times within 7 days of culturing. After reaching the recommended density, cells were lifted with trypsin-EDTA (Gibco-LifeSciences, Gaithersburg, Md.) and centrifuged at 200×g for 10 minutes to form a cell pellet. Cells collected in a cell pellet were re-suspended in RoosterNourish media at a concentration of 10 million cells/mL. Approximately 1 million cells were seeded onto each scaffold by adding 100 µL of concentration cell solution to cover the scaffold. Scaffolds were kept at 37° C. for 4 hours to allow for attachment to the scaffold surface. Cell culture media was changed every other day for cell maintenance.

Staining and Confocal Imaging

Live/dead assays were used to assess cell viability and morphology. Scaffolds were washed with Hank's buffered saline solution (HBSS, Life Technologies, Carlsbad, Calif.) for 5 minutes to remove excess media and other reagents. Cells on the scaffolds were stained with 2 µM ethidium homodimer and 4 µM calcein AM (Life Technologies, Carlsbad, Calif.) combined with HBSS and incubated for 30 minutes in the dark. Scaffolds were then washed with HBSS, soaked in 200 µL of 4% paraformaldehyde for each scaffold, and left to incubate for 15 minutes. Scaffolds were washed with 200 µL of phosphate-buffered saline (PBS) and stored in PBS until they could be imaged using a confocal microscope.

DNA Quantification hMSCs were lifted from scaffolds using trypsin-EDTA (Gibco-LifeSciences, Gaithersburg, Md.) and centrifuged into a cell pellet. DNA was isolated from the hMSCs using a DNeasy Plus MiniKit (Qiagen, Frederick, Md.). DNA was quantified using a PICOGREEN™ dsDNA Assay Kit (Quanti-iT, ThermoFisher Scientific, Waltham, Mass.). DNA isolates from the DNeasy kit were normalized to standard curve generated from the PICOGREEN™ dsDNA Assay to quantify DNA amounts.

Centrifugation Device Fabrication

Lid Fabrication: A lid was designed using SOLID-WORKS® software (Dassault Systémes, Vélizy-Villacoublay, France) for a slight press fit into the inner wells of a standard 24 well plate (FIG. 4), allowing the assembly to be flipped upside down and centrifuged. The device was designed to capture the scaffolds and cell solution during centrifugation. The lid was fabricated using an ENVISION-TEC® Perfactory 4 Mini Multilens using E-SHELL® 300 (EnvisionTEC, Inc., Dearborn, Mich.), a biocompatible acrylate-based resin. Excess resin was removed by submerging printed objects in 99% isopropanol (Pharmco-Aaper, Shelbyville, Ky.) for 5 minutes and blowing the interior dry with air. Complete resin curing was achieved with 1000 flashes of broad spectrum light (Otoflash, EnvisionTEC, Inc., Dearborn, Mich.). The printed lid was cleaned in 100% ethanol (Pharmco-Aaper, Shelbyville, Ky.) for more than 30 minutes to leach any remaining soluble contaminants. Before use, the lid was sterilized under 100% ethanol and UV light for 20 minutes. Afterwards, the lid was rehydrated in a serial rehydration to pH 7.4 sterile PBS in 4 steps (75:25, 50:50, 25:75, and 0:100 ethanol:PBS), with each intermediary step allowed to soak for 5 minutes.

Bone Marrow Seeding

Whole human unprocessed bone marrow (Lonza, Walkersville, Md.) was seeded onto the printed scaffolds placed in ultra-low attachment 24-well plate (Thermo Fisher Scientific, Waltham, Mass.). Equal amount of Dulbecco's modified Eagle's medium (Life Technologies, Gaithersburg, Md.) supplemented with 1.0% v/v penicillin/streptomycin (Life Technologies, Gaithersburg, Md.) and 0.1 mM nonessential amino acids (Life Technologies, Gaithersburg, Md.) was added to each well. The plate was incubated at 37° C., 5% $CO_2$, and 80% humidity for 24 hours to allow attachment.

Centrifugation Assay

Figure 4:
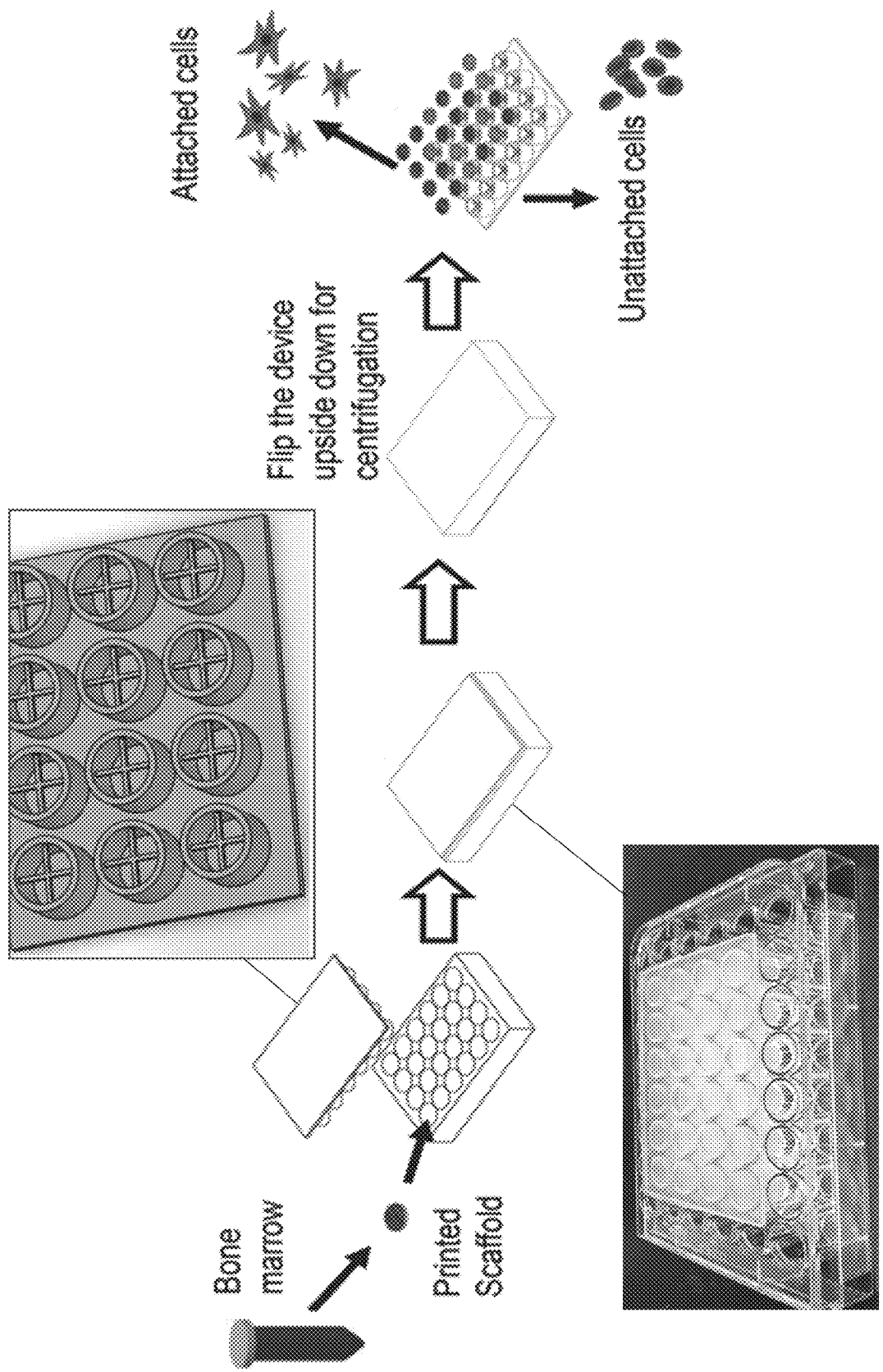
FIG. 4 illustrates a centrifugation system in accordance with the present disclosure for evaluating cell adhesion and adhered cell phenotype. Panel A shows the set-up of the centrifugation assay system for scaffolds seeded with whole bone marrow. The upper inset is a CAD image showing the configuration of a portion of the lid for use with the centrifugation system in accordance with disclosed embodiments. The lower inset is an image of the lid (showing 24 well version) covering and secured to the plate wells. The 3D-printed lid is applied to separate the adhered and non-adhered cells.

The centrifugation assay system set up is shown in FIG. 4, Panel A. The concept and determination of the centrifugal force were based on previously established protocol (Ferlin, K. M. et al. "*Separation of Mesenchymal Stem Cells Through a Strategic Centrifugation Protocol*," Tissue Engineering Part C-Methods 22(4):348-359). The 3D printed cover (FIG. 4, upper inset) was applied to seal the wells of the 24-well plate (FIG. 4, lower inset) in place of the original lid. The plates were centrifuged upside down at a relative centrifugal force of 50 g for 5 min at 22° C. to separate the adhered and non-adhered cells. After first centrifugation, the supernatant containing the non-adhered fraction was collected and enumerated. Gibco Trypsin-EDTA (Gibco-Life-Sciences, Gaithersburg, Md.) was added, centrifuged again to harvest, and scaffolds and wells washed once with PBS to lift the adhered fraction.

Evaluation of hMSCs Isolated from Whole Bone Marrow

Flow cytometry was conducted to analyze the cell population isolated from the bone marrow. The cells were resuspended at a concentration of approximately 5 million/mL. Cells and controls were stained using Human MSC Analysis Kit (BD STEMFLOW™; Becton, Dickinson and Co., Franklin Lakes, N.J.) following the manufacturer's instruction. The data was analyzed using FLOWJO™ (FlowJo LLC, Ashland, Oreg.) to gate the populations. Briefly, 100 µL of each sample was mixed with 20 µL of the hMSC Positive Cocktail (CD90 FITC, CD73 APC, and CD105 PerCP-Cy5.5) and 20 µL of the hMSC Negative Cocktail (CD34 PE, CD45 PE, CD11b PE, CD19 PE, and HLA-DR PE) and incubated at 4° C. in the dark for 30 min. The mixed cell suspensions were washed twice with 500 µL of PBS containing 1% bovine serum albumin (BSA). The cells were suspended in 500 µL of PBS containing 1% BSA and analyzed using a BD FACSCANTO II™ cell analyzer (Becton, Dickinson and Co., Franklin Lakes, N.J.). The positive control using hMSCs (Lonza, Walkersville, Md.) and the negative isotype controls was used to set up the gate for all samples. Cells of each group were counted during 90-second run at medium rate, as controlled volume.

Figure 6:
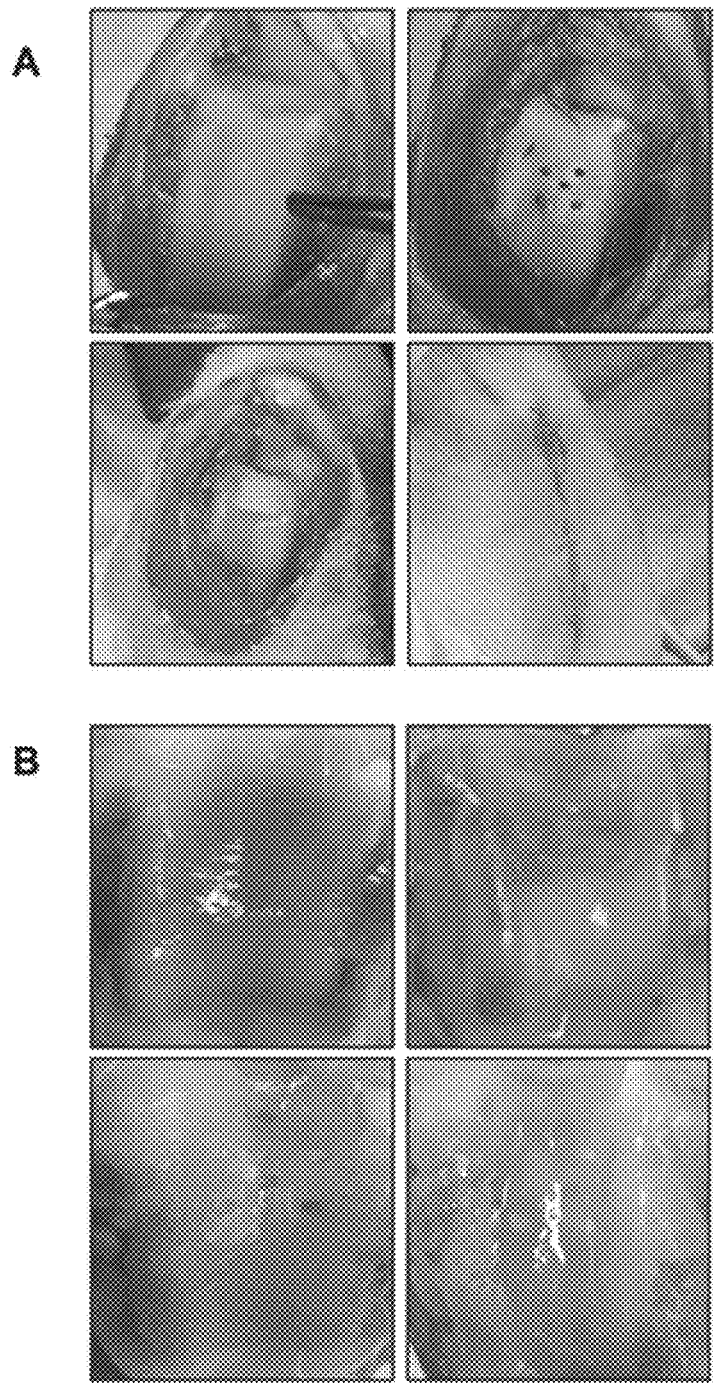
FIG. 6 shows animal surgery and locomotion evaluation. Panel A shows images of the surgical procedure of microfracture and scaffold implantation. A 3 mm×3 mm full thickness defect was made in the center of the trochlear groove (Panel A, top left); 5 small holes (0.75 mm) were drilled at the four corners and the center of the defect on the subchondral bone (Panel A, top right); scaffold with the defect size covered the defect area (Panel A, bottom left); the exposed patellar groove was reverted and the wound was closed by buried absorbable suture (Panel A, bottom right). Panel B shows images of the harvested joints after 8 weeks showing regenerated cartilage tissue, including: defect without treatment (Panel B, top left); defect treated by microfracture (Panel B, top right); defect treated by microfracture and PLCL scaffold (Panel B, bottom left); and defect treated by microfracture and PLCL-aggrecan scaffold (Panel B, bottom right).

Animal Surgery and Tissue Harvest 14 female New Zealand White Rabbits (NZW, 7-9 lb) (Covance Inc., Princeton, N.J.) were anesthetized with Ketamine (35-40 mg/kg)/Xylazine (2-5 mg/kg). A total of four groups were evaluated including: i) defect control group; ii) microfracture only group; iii) microfracture with unmodified scaffold group; and iv) microfracture with aggrecan-functionalized scaffold group. Three rabbits were included in each group, with one extra in the groups treated with scaffold as a preparation for potential unknown side effects. Post sedation isoflurane delivered from a precision vaporizer (1.5-3%) in 100% 02 was administered via face mask during the surgery. The right hind leg served as the defect limb while the left hind leg was not treated in this unilateral defect model. A midline knee incision was made and a medial parapatellar approach performed to the knee. The patella was dislocated laterally to expose the articular surface of the trochlea. Bupivacaine 0.25% (up to 2 mg/kg) was injected to the trochlear grove prior to patella dislocation as local analgesia. A full thickness cartilage defect in the center of the trochlear groove was created that measured approximately 3 mm in length and width. In the microfracture groups, five holes were drilled to a ~8 mm depth with a 0.75 mm K-wire. In the two experimental scaffold groups, modified or unmodified polymer constructs were inserted into the cartilage defect site and secured with fibrin glue (TISSEEL™; Baxter, Deerfield, Ill.). Scaffold implants were fabricated as described above; however, due to the relatively thin cartilage tissue present in the rabbit model (~500 micron), the scaffold implant utilized for the animal study included the top zone scaffold structure (FIG. 3C). The knee was taken through several cycles of range of motion and the fibrin glue/construct complex was found to be intact. The patella was then reduced and the incision closed with absorbable sutures (FIG. 6).

The joints from both knees were harvested after 8 weeks. The left knee tissue was used as healthy control in the evaluation assays. Euthanasia was performed with Beuthasol (Pentobarbital IV, 100 mg/kg) in the auricular vein after a ketamine 20-40 mg/kg and 2-5 mg/kg xylazine subcutaneous injection. After euthanasia, the bilateral knee joints (femur end and chondyle) were harvested for further analysis. The animal study, including the locomotion test (protocol #0717009), was approved by Institutional Animal Care and Use Committee (IACUC) at University of Maryland, School of Medicine, Baltimore, Md. All animal studies including the follow up evaluation were conducted as blind tests.

Animal Locomotion Test and Evaluation

Figure 7:
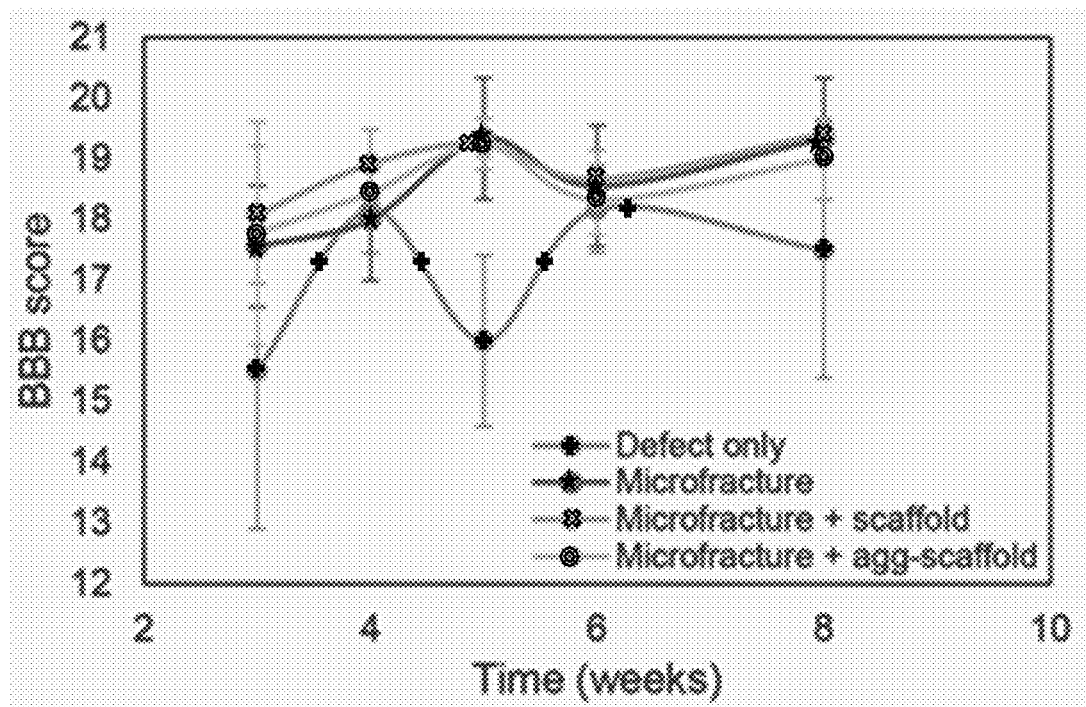
FIG. 7 illustrates graphically BBB score evaluation over the 8 weeks of post-surgery observation in open field locomotion test. Compared to defect control, all subjects with surgical treatment showed improved score overtime. The mobility of the animals was not negatively affected by the addition of the implantation.
Figure 8:
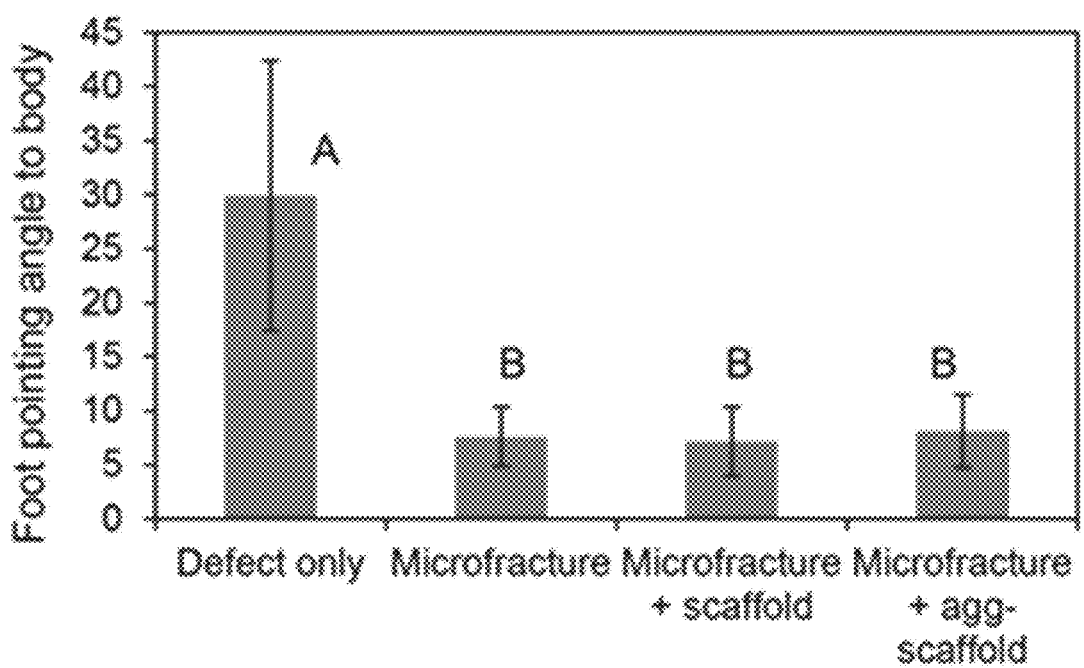
FIG. 8 illustrates graphically measurement results of foot alignment during movement. All experimental groups displayed smaller foot pointing angle, indicating a healthier walking pattern during recovery. N=3. Data is shown as mean±standard deviation. ANOVA was performed to compare the significance among groups. Means that do not share the same letter are significantly different.

After two weeks (starting on week 3 following surgery recovery per veterinarian advice), the rabbits were taken to an open field restricted by a 1.4 m×0.5 m fence to allow for locomotion evaluation. Videos were recorded of test subjects from the top and side view on weeks 3, 4, 5, 6, and 8 post-surgery. Videos were analyzed and test subjects were evaluated by a modified Basso, Beattie, and Bresnahan (BBB) Locomotor Rating Scale (Table 1) to quantify the subjects' movement, coordination, and weight bearing abilities (FIGS. 7-8). The score was averaged from three evaluators with a blind study.

TABLE 1

Modified BBB Locomotor Rating Scale for Rabbits after Orthopedic Surgery

| | |
|---|---|
| 0 | No observable movement of the hindlimbs. |
| 1 | Slight (limited) movement of one or two joints, usually hip and/or knee. |
| 2 | Extensive movement of one joint or extensive movement of one joint and slight movement of the other. |
| 3 | Extensive movement of two joints. |
| 4 | Slight movement of all three joints of the hindlimb (HL). |
| 5 | Slight movement of two joints and extensive movement of the third joint. |
| 6 | Extensive movement of two joints and slight movement of the third joint. |
| 7 | Extensive movement of the three joints in the hindlimbs. |

TABLE 1-continued

Modified BBB Locomotor Rating Scale for Rabbits after Orthopedic Surgery

8 Sweeping without weight bearing or plantar support of the paw without weight bearing.
9 Plantar support of the paw with weight bearing only in the support stage (i.e., when static) or occasional, frequent or inconsistent dorsal stepping with weight bearing and no plantar stepping.
10 Plantar stepping with occasional weight bearing and no forelimb (FL)-HL coordination.
11 Plantar stepping with frequent to consistent weight bearing and no FL-HL coordination.
12 Plantar stepping with frequent to consistent weight bearing and occasional FL-HL coordination.
13 Plantar stepping with frequent to consistent weight bearing and frequent FL-HL coordination.
14 Plantar stepping with consistent weight support, consistent FL-HL coordination and predominantly rotated paw position (internally or externally) during locomotion both at the instant of initial contact with the surface or frequent plantar stepping, consistent FL-HL coordination and occasional dorsal stepping.
15 Consistent plantar stepping, consistent FL-HL coordination; predominant paw position is parallel to the body at the time of initial contact.
16 Consistent plantar stepping and FL-HL coordination during gait; the predominant paw position is parallel to the body at the time of initial contact and curved at the instant of movement.
17 Consistent plantar stepping and FL-HL coordination during gait; the predominant paw position is parallel to the body at the time of initial contact and at the instant of movement.
18 Consistent plantar stepping and FL-HL coordination during gait; the predominant paw position is parallel to the body at the time of initial contact and curved during movement. The animal presents partial standing.
19 Consistent plantar stepping and FL-HL coordination during gait; the predominant paw position is parallel to the body at the instant of contact and at the time of movement, and the animal presents occasionally full standing.
20 Consistent plantar stepping and FL-HL coordination during gait; the predominant paw position is parallel to the body at the instant of contact and at the time of movement, and the animal presents frequent full standing.
21 Consistent plantar stepping and coordinated gait, consistent movement; paw position is predominantly parallel to the body during the whole support stage; consistent full standing.

Definitions:
Slight: partial joint movement through less than half the range of joint motion.
Extensive: movement through more than half of the range of joint motion.
Sweeping: rhythmic movement of HL in which all three joints are extended, then fully flex and extend again; animal is usually side lying, the plantar surface of paw may or may not contact the ground; no weight support across the HL is evident.
No Weight Support: no contraction of the extensor muscles of the HL during plantar placement of the paw; or no elevation of the hindquarter.
Weight Support: contraction of the extensor muscles of the HL during plantar placement of the paw, or elevation of the hindquarter.
Plantar Stepping: The paw is in plantar contact with weight support then the HL is advanced forward and plantar contact with weight support is reestablished.
Dorsal Stepping: weight is supported through the dorsal surface of the paw at some point in the step cycle.
FL-HL Coordination: for every FL step an HL step is taken and the HLs alternate.
Occasional: less than or equal to half.
Frequent: more than half but not always; 51-94%.
Consistent: nearly always or always; 95-100%.
Partial standing: lifting the forelimb off the ground but with trouble holding the body straight for more than 1 second.
Full standing: lifting the forelimb off the ground with a full support provided by the hindlimb.

Optical Coherence Tomography (OCT)

Figure 9:
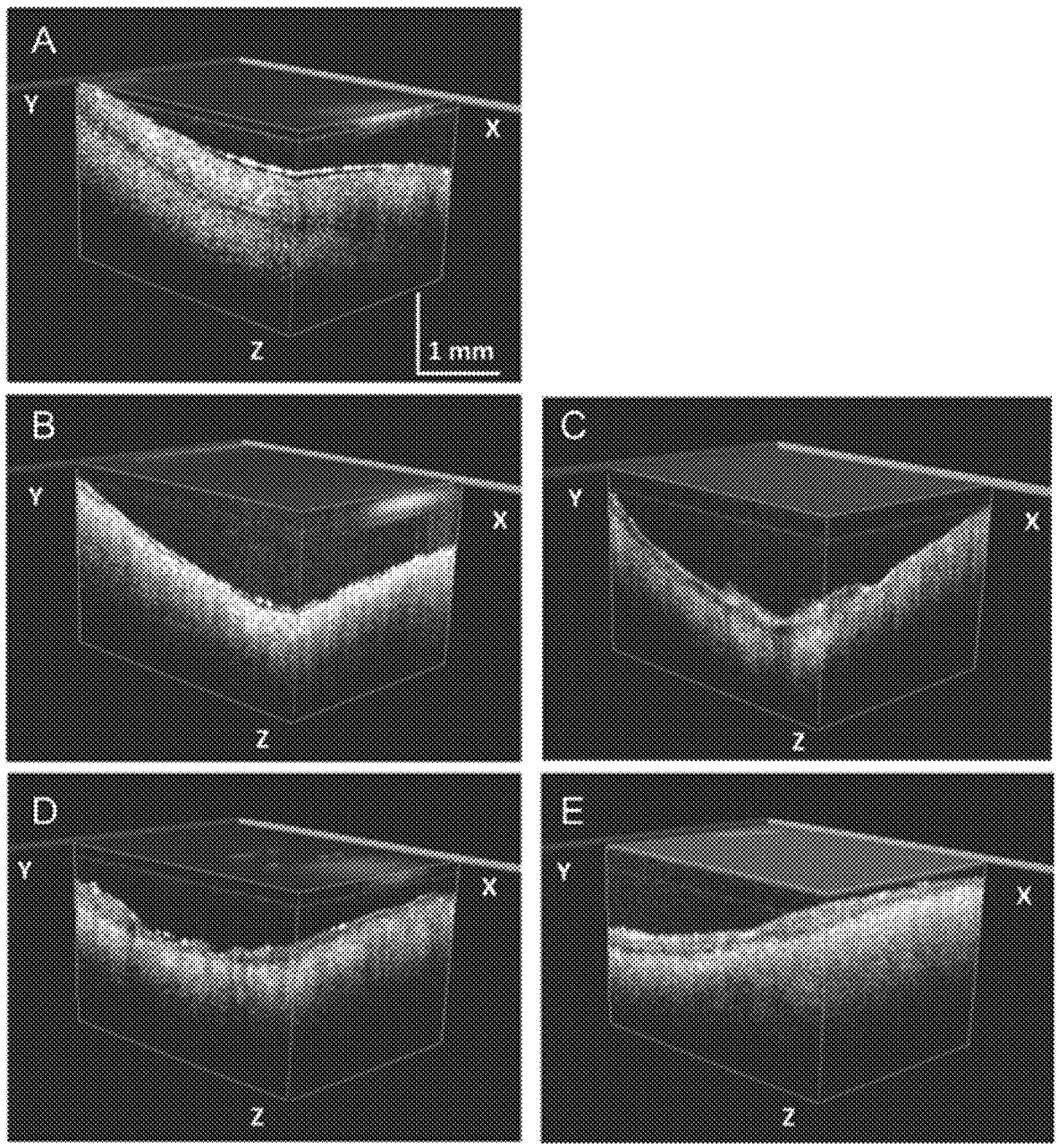
FIG. 9 shows 3D OCT images of cartilage and thickness quantification. The representative images of groups include: Healthy control group (Panel A); Defect control group (Panel B); Microfracture group (Panel C); Microfracture and PLCL scaffold group (Panel D); and Microfracture and Aggrecan-PLCL scaffold group (Panel E).

The frequency-domain OCT imaging system was equipped with a wavelength-swept laser light source centered at 1310 nm with 100 nm bandwidth (Tang, Q. et al. (2016) "Depth-resolved imaging of colon tumor using optical coherence tomography and fluorescence laminar optical tomography," Biomedical optics express 7(12):5218-5232). The wavelength-swept frequency was 16 kHz and the output power was 17 mW. 3% of the laser output power went into a Mach-Zehnder interferometer and generated a frequency-clock signal with uniformly spaced optical frequency to trigger sampling the OCT signal. The system applied a fiber-based Michelson interferometer and about 97% of the laser power was split evenly to the sample and reference arms of the interferometer. The signals reflected from the sample and reference arms encountered at the fiber couple and formed interference fringes, which encoded different frequencies, were then received by a balanced detector. Depth-resolved tomography was achieved by performing a fast Fourier transform of the interference fringes (Tang, Q. et al. (2014) "Real-time epidural anesthesia guidance using optical coherence tomography needle probe," Quantitative Imaging in Medicine and Surgery 5(1):118-124). The scanning field of view (FOV) was set at 5 mm×5 mm to cover the entire defect area with 800 pixels in each direction (FIG. 9). During imaging, the tissue was irrigated with PBS to prevent dehydration. For cartilage thickness analysis on the acquired images (FIG. 10), 10 random sections were picked on the X-axis (cross-section from top of trochlea groove) and the thickness of each section was calculated from a random point on the Y-axis. The average thickness of each group was calculated from all biological samples of the group.

Histological Staining and Image Analysis

After harvesting and OCT scanning, tissue samples were fixed in buffered 4% paraformaldehyde solution containing 1% sucrose. Samples were decalcified, dehydrated, and embedded in paraffin. The samples were sectioned to 5 μm thick slices and placed on positively charged glass slides. For H & E staining (FIG. 12), the samples were stained by hematoxylin, followed by counterstaining of eosin. For Alcian Blue staining (FIG. 11), samples were stained by Alcian Blue for 30 minutes, then counterstained under nuclear fast red for 5 minutes. The images were taken using an Nikon ECLIPSE Ti2™ research microscope (Nikon, Tokyo, Japan) mounted with a Nikon DS Ri2™ high-definition color camera (Nikon, Tokyo, Japan). The images were analyzed using the automatic measurement tools built into the microscope software. Chondrocyte number was counted in the H & E images (FIG. 12, Panel F) by thresholding the RGB color. Circularity (0.33-1.00) and area (_3.93) were applied as restrictions to determine cell nuclei. For safranin-O staining, after deparaffinization and hydration, the slides were stained with hematoxylin, fast green, and 0.1% safranin-O solution following standard procedures. Immunohistology was conducted using type II collagen antibody (Abcam, Cambridge, UK) following standard protocol. Similar thresholding techniques were applied when quantifying the type II collagen expression. The binary area of Alcian Blue stained GAGs (FIG. 11, Panel F) was quantified by adjusting hue, saturation and intensity (HSI) values. Area (0.05-13807 μm$^2$) was applied as a restrictive factor to eliminate noise and background. Statistical significance was generated for all three subjects in each group during quantification. In the image analysis, the healthy control image was used to set thresholds and restrictions and applied to all images.

Results and Further Discussion

Aggrecan Functionalization and In Vitro Evaluation of Cell Adhesion

Figure 3:
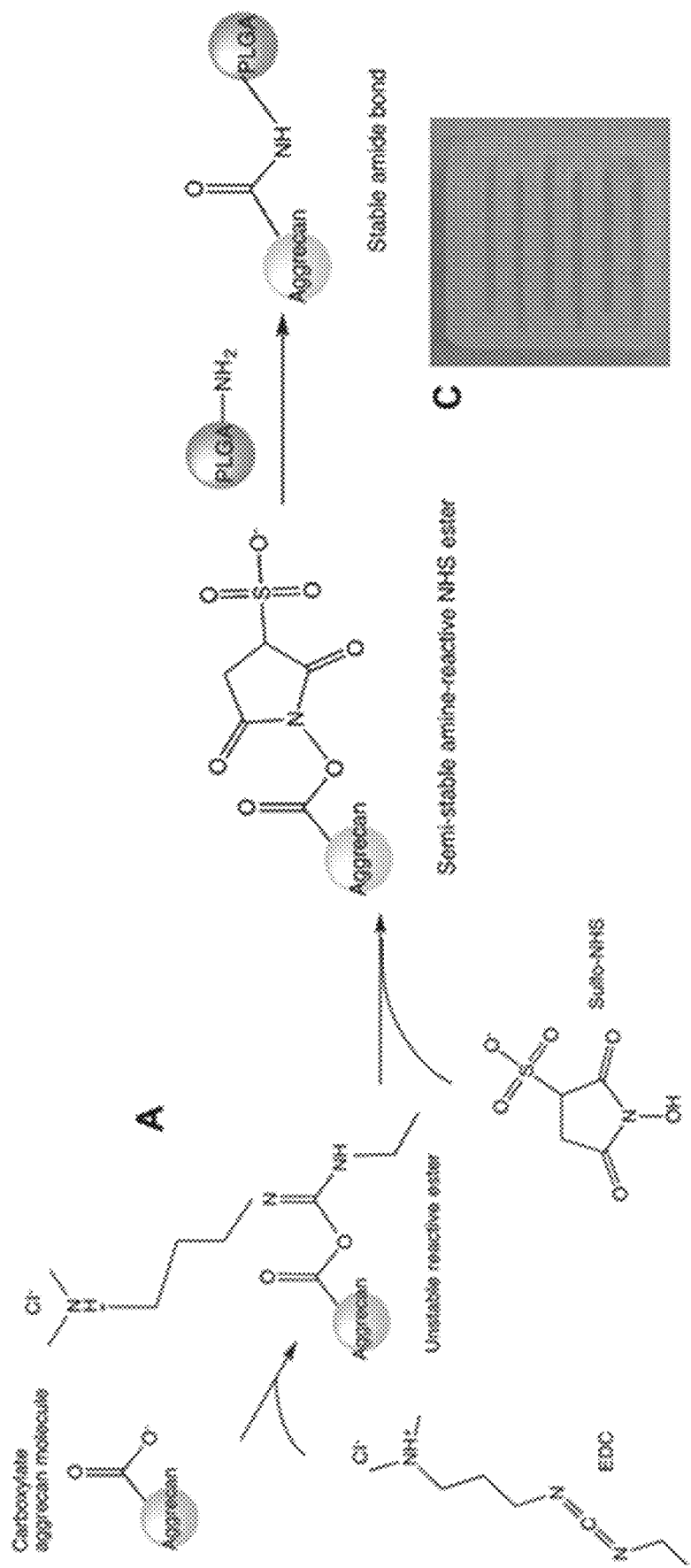
FIG. 3 illustrates the design and characterization of aggrecan functionalization on a PLCL scaffold in accordance with the present disclosure. Panel A shows a schematic diagram of chemical reaction between aggrecan and PLCL-amine scaffold using EDC and sulfo-NHS. Panel B shows NMR spectrum confirming the presence of amine group after 3D printing the blended PLCL and PLGA-amine material and aggrecan modification; X-axis shows chemical shift (ppm). Panel C shows an image of 3D-printed amine-PLCL scaffold layer with dimensions of 3 mm (length)×3 mm (width)×1 mm (height). Panel D illustrates graphically DNA quantification of hMSCs seeded on PLCL, PLCL-amine, and PLCL-aggrecan scaffold after 7 days. Significantly higher DNA concentration was observed with the aggrecan functionalization. N=3; data is shown as mean±standard deviation. *Shows statistically significant difference. Panel E illustrates graphically a comparison of compressive modulus of wet PLCL scaffold and PLCL-aggrecan scaffold. The modulus of the two groups showed statistically significant difference based on t-test ($p<0.05$). N=6 in each group.
Figure 3:
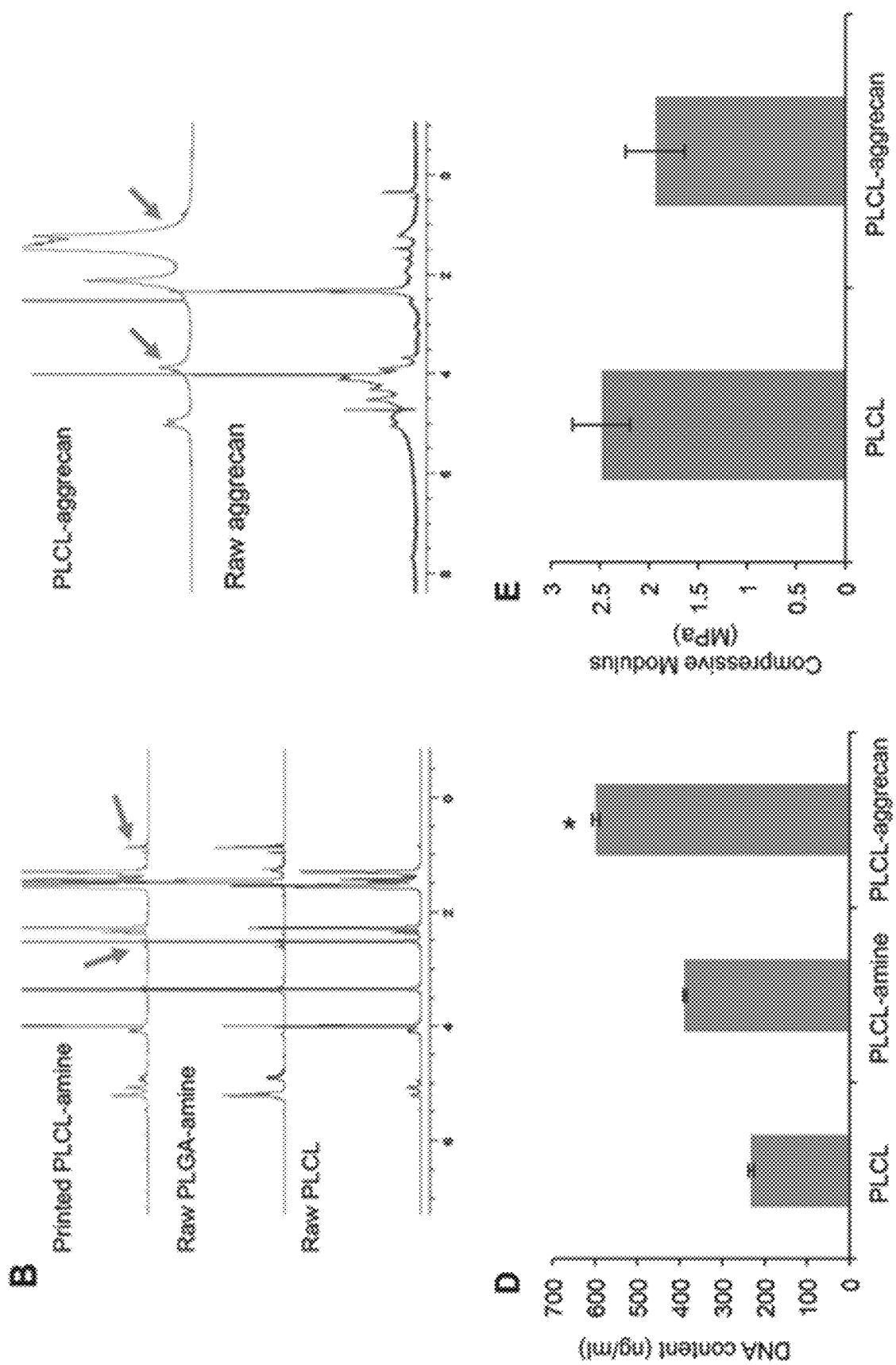

The EDC-NHS reaction to covalently bind the carboxyl groups on the side chains of aggrecan and the amine groups on the printed PLCL-amine scaffold is shown in FIG. 3, Panel A. After chemical reaction, the modified scaffold sample was compared to PLCL and PLCL-amine samples using NMR. First, by comparing the spectra of printed plain PLCL sample, raw PLGA-amine, and printed PLCL-amine sample (blended with 85% PLCL and 15% PLGA-amine), we demonstrated that the amine group is preserved during the printing process (FIG. 3, Panel B). Chemical shift was expressed in parts per million (ppm). Amine shift at 0.93 ppm and 2.61 ppm were observed in the PLCL-amine sample. Further analysis on PLCL-amine sample, pure aggrecan sample, and the functionalized sample revealed matching peaks confirming the presence of aggrecan (FIG. 3, Panel B). Because aggrecan's complex structure, the acquisition of separate peaks was challenging. Low $^1$H signal was due to low aggrecan solubility as a large proteoglycan molecule. After solvent suppression, the matched peaks were primarily observed at 3.94 ppm, sulfate, and 1.5 ppm, carboxylic ester; these two groups are the most abundant side groups in aggrecan. Interestingly, the addition of aggrecan was demonstrated to have an impact on the compressive modulus of the wet scaffold. The Young's modulus of printed PLCL-amine scaffold and aggrecan functionalized scaffold were 2.48±0.29 MPa and 1.93±0.30 MPa, respectively (FIG. 3, Panel E).

After confirming the presence of functional groups on the scaffold, the biological response of surface modifying the scaffolds was evaluated. hMSCs were seeded onto PLCL scaffold, PLCL-amine scaffold, and aggrecan modified scaffold. The three groups presented DNA concentrations of 231.91±5.73 ng/ml, 386.86±3.73 ng/ml, and 597.24±8.02 ng/ml, respectively. From the DNA quantification data, after 7 days the aggrecan modified scaffold showed three times more DNA content than the unmodified scaffold (FIG. 3, Panel D), indicating that the aggrecan bond to the scaffold played an important role in improving cell attachment. Although the PLCL-amine group showed a higher DNA content than the PLCL group in the presented graph, further experiments indicated that the difference between PLCL-amine group and the PLCL group was not significant.

After demonstrating that aggrecan functionalization improved cell attachment, whole bone marrow was seeded onto the scaffold to evaluate the attached cell population. A cell centrifugation assay isolated the adhered cells from whole bone marrow to determine cell phenotype through flow cytometry (FIG. 4, Panel A). By incorporating a 3D printed lid that can air seal the 24-well plate with designed features for this experiment, the non-adhered and adhered cell populations were separated for further analysis. A hMSC cocktail was used in the flow cytometry to identify the hMSCs population (CD105+, CD90+, CD73+, CD11b−, CD19−, CD45−, HLA-DR−). The adhered population is approximately 0.1% of all cells in the whole bone marrow, according to both flow counting and hemocytometer counting. The aggrecan modified scaffold had approximately 10 times more adhered cells than the control groups (PLCL and PLCL-amine scaffolds).

Figure 5:
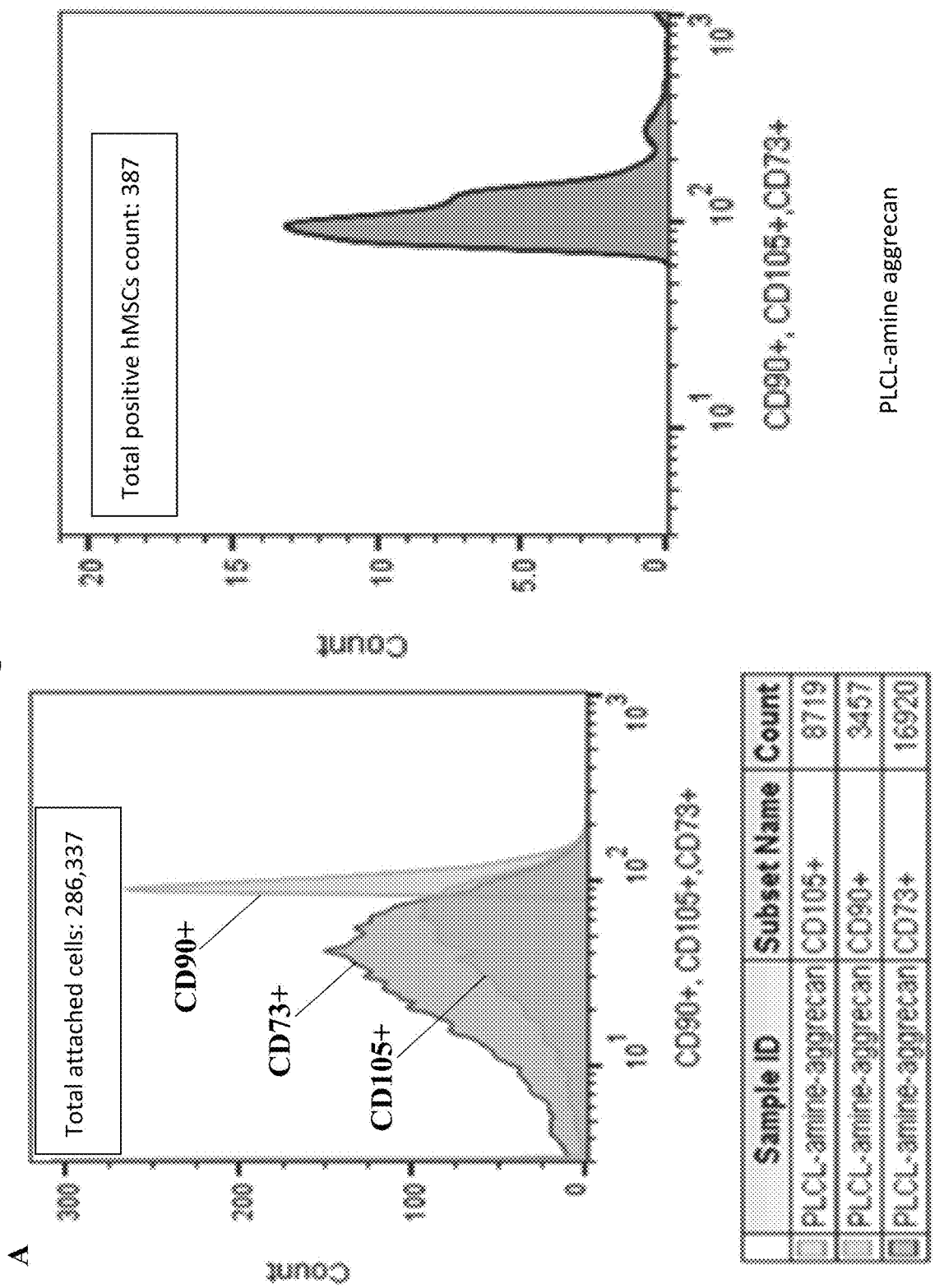
FIG. 5 shows flow cytometry analysis of the adhered cell populations to PLCL-amine-aggrecan scaffold (Panel A), PLCL-amine scaffold (Panel B), and PLCL scaffold (Panel C). The overlapped graphical area based on three positive markers (CD90+, CD105+, CD73+) was further quantified to count positive hMSCs. With the addition of aggrecan, total attached cell number was improved by approximately 10 times. More positive hMSCs number was present with aggrecan modification due to overall increased cell number.
Figure 5:
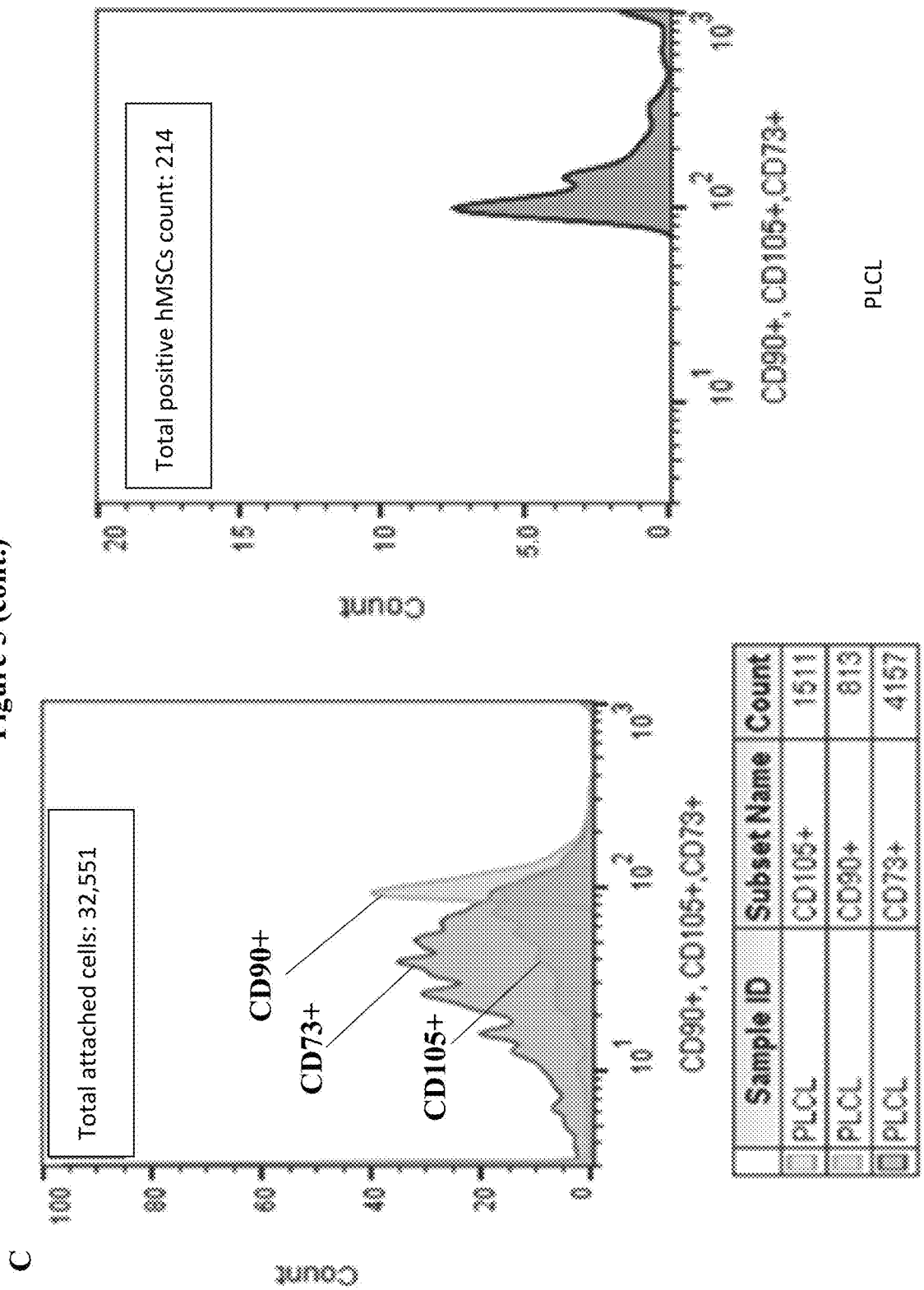

The adhered/attached cell count in controlled 90 second flow for PLCL-amine-aggrecan modified scaffold, PLCL-amine scaffold, and PLCL scaffold was 286377, 21113, and 32551, respectively (FIG. 5, Panels A-C). Among the adhered cells, the positive hMSCs for aggrecan modified scaffold and the two controls are 387, 200 and 214 in a controlled unit volume, which yields a positive hMSC percentile of 0.1-1% among the adhered cells in the whole bone marrow. This percentage matches the commonly reported hMSCs percentile in human whole marrow, thereby demonstrating sufficiency of the isolation technique using the disclosed centrifugation assay with 3D printed lid.

In Vivo Assessment of Scaffold Function

The above experiments demonstrated substantially improved cell recruitment as a result of aggrecan functionalization. The actual healing process associated with microfracture is more difficult to mimic in the in vitro environment. Accordingly, the animal model was used to further test the therapeutic effect of the scaffold. The animal surgery was completed successfully following the approved protocol. All 14 rabbits survived with overall good health condition until the termination of the study. The knee joints were harvested after 8 weeks for further analysis including tissue evaluation, OCT scanning and histology. The implanted scaffolds were mostly degraded after 8 weeks. A thin layer of regenerated cartilage tissue visibly appeared to cover the defect area in the experimental groups. With the additional scaffold, and especially when functionalized, the newly regenerated cartilage tissue showed a much healthier appearance (FIG. 6, Panel B).

In the locomotion test, rabbit movement was recorded at each time point from both side view and top view throughout the eight week observation period. The locomotion behavior was evaluated using a modified BBB score scale as described above. While the defect control group demonstrated no movement improvement over the course of the study, all experimental groups showed an increasing trend of scores. Rabbits treated with aggrecan functionalized scaffold or plain scaffold had comparable scores with rabbits treated with traditional microfracture. In this study, with modified BBB score to better represent the rabbit locomotion behavior, all rabbits received a score higher than 13 (out of 21). Considering the relatively good recovery observed with regard to movement ability with treatments, no significant differences among the experimental groups were observed at each time point. All experimental groups with treatments had an average score of around 19 on week eight (FIG. 7). In addition, images were captured to assess the foot pointing angle relative to the rabbit's body. If the rabbit's movement was affected by pain or impaired joint function, they would apply unbalanced force on their hind limb or drag the limb when walking. This is reflected by the angle of the surgical site hind limb to their body. From the analysis, all groups with treatment showed a significantly smaller angle as compared to the defect control group, indicating a healthier walking pattern (FIG. 8). The implantation groups showed statistically similar small angles (less than 10°) compared to the microfracture group, indicating that the scaffold did not cause discomfort during movement.

Figure 10:
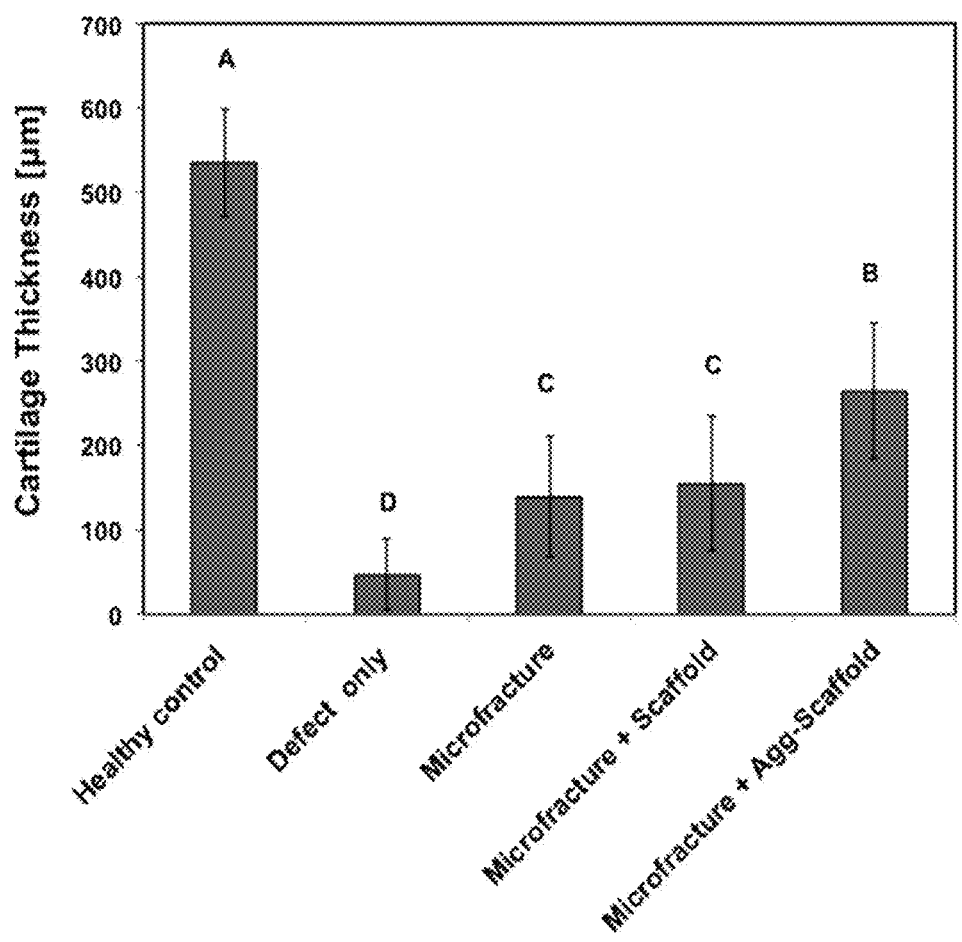
FIG. 10 shows graphically differences in cartilage thickness between the groups: Healthy control group; Defect control group; Microfracture group; Microfracture and PLCL scaffold group; and Microfracture and Aggrecan-PLCL scaffold group. For each group, cartilage thickness was calculated from 10 randomly selected sections along y-axis (see FIG. 9). On each section, a random position on x-axis was selected for calculation. The average and standard deviation of the thickness in the plot was calculated from all samples in each group. Aggrecan functionalization resulted in a much thicker regenerated cartilage layer with more homogenous 3D thickness distribution as compared to the conventional or normal microfracture procedure and the group treated with unmodified scaffold. N=3. Data is shown as mean±standard deviation. Groups that do not share the same letter are significantly different ($p<0.05$).

After 8 weeks, the femur end of the joints was harvested for OCT scanning and histological analysis (FIG. 9). A 5 mm×5 mm scanning area was used to ensure the coverage of the entire defect area. Clinically, cartilage thickness is a factor in assessing the degree of osteoarthritis. Thus, thickness was measured to evaluate the regeneration potential of different treatments (FIG. 10). OCT presents advantages on resolution by measuring the intensity of reflected infrared light instead of sound, and has been used as an non-invasive method to assess the tissue both qualitatively and quantitatively including study on rabbit cartilage. The bone and cartilage boundary was determined by the reflected light contrast due to different tissue structures (Rogowska, J. et al. (2003) "*Cartilage thickness measurements from optical coherence tomography*," J Optical Society of America a-Optics Image Science and Vision 20(2):357-367). The healthy control sample was used as a reference to determine the scan settings, and the outer and inner boundary of cartilage tissue. Images revealed that aggrecan-functionalized scaffolds resulted in a more homogenous thickness distribution (FIG. 9, Panel E). This difference, compared to the non-treated scaffold, indicates better integration with the newly regenerated tissue as a result of the biological activity provided by aggrecan. The released cells and growth factors from bone marrow were likely better preserved through the proteoglycan support. Furthermore, the average regenerated cartilage thickness of samples in the aggrecan-PLCL treatment group was 264±80 µm, which is significantly higher than all other groups. The samples from the defect control group, microfracture treatment group, and PLCL scaffold group showed regenerated thickness of 47±41 µm, 139±72 µm, and 155±80 µm, respectively (FIG. 9, Panels B-E). These results demonstrate the beneficial therapeutic effect of functionalizing the scaffold with aggrecan. Moreover, the combination of microfracture with the acellular bioactive scaffold resulted in a substantially improved cartilage regeneration in 8 weeks.

Histological staining was performed for the harvested joints after embedding and decalcification. In the H & E staining, the nuclei were stained dark purple by hematoxylin and the eosinophilic structures mainly composed of intracellular and extracellular proteins were counterstained by eosin Y as pink. The regenerated cartilage tissue appeared as lighter pink compared to the subchondral bone tissue (FIG. 12). Chondrocyte number in the cartilage layer was quantified using the Nikon Ti2 built-in analysis tool. The healthy control was used to set the color threshold and restrictions (circularity and area) to identify the cell nuclei. The defect control group showed very limited regenerated tissue with only 55±26 chondrocytes in the imaging area. The microfracture treated group and the PLCL scaffold group showed a similar amount of newly formed tissue with a chondrocytes count of 112±26 and 134±95, respectively. The slightly improved regeneration of the non-treated scaffold is possibly caused by the initial support provided by the implant. However, the poor integration with the local tissue limited the positive effect. With the addition of aggrecan, the tissue formation was significantly improved with almost three times more chondrocytes (366±95) present in the cartilage layer (FIG. 12, Panel F).

The Alcian blue staining further confirmed the therapeutic effect of the aggrecan-functionalized scaffold (FIG. 11). As a major component of native cartilage, the production of glycosaminoglycans (GAGs) by chondrocytes may be used to assess the chondrogenesis or cartilage tissue regeneration. As shown by the data, the GAG content stained by Alcian blue was greatly enhanced with the support of scaffold. The GAG expression was quantified as binary area ($\mu m^2$) in each image (FIG. 11, Panel F). The calculated average GAG contents of samples from defect group, microfracture group, PLCL scaffold group and aggrecan-PLCL scaffold group were 4412±940 $\mu m^2$, 21052±22064 $\mu m^2$, 380120±32307 $\mu m^2$, and 92603±30177 $\mu m^2$, respectively.

Figure 13:
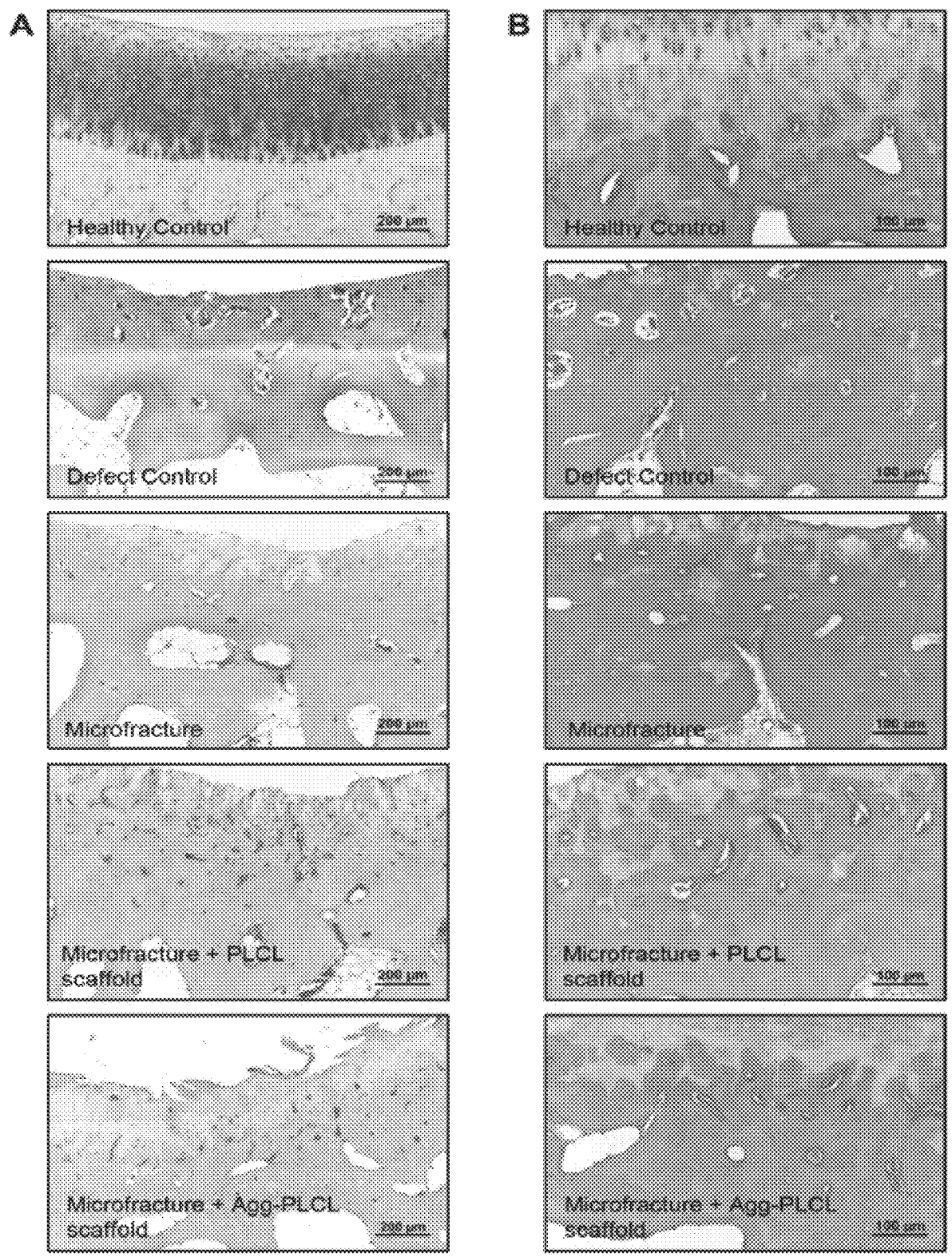
FIG. 13 shows images from an histological evaluation of the cartilage-bone interface. Panel A shows images from Safranin-O staining showing GAG production in the regenerated cartilage. The red safranin-O stain is proportional to the proteoglycan content, while Fast Green counterstains the non-collagen sites and provides a clear contrast to the safranin-O staining. Panel B shows images from H & E staining at higher magnification (20×) showing the subchondral bone region underneath the defect area. Compared to the healthy control, all groups displayed normal subchondral bone tissue with high density. From top to bottom in each of Panels A and B, representative images show: Healthy control; Defect control; Microfracture only; Microfracture+PLCL scaffold; and Microfracture+PLCL-aggrecan scaffold for both staining.

The aggrecan functionalization resulted in 20 times more GAG production than the non-treated group and 4.4 times more GAG production compared to the microfracture treatment. The production of proteoglycan is proportional to the safranin-O staining in normal cartilage. The healthy control showed a strong affinity to safranin-O to form a red complex with a top layer of counter stained green color. Compared with regular microfracture treatment, the scaffold treatment showed a higher level of proteoglycans, although safranin-O was reported as a not very sensitive indicator when the GAGs were depleted, for example, in the newly formed tissue layer (FIG. 12, Panel A) (see, e.g., Schmitz, N. et al. (2010) "*Basic methods in histopathology of joint tissues*," Osteoarthritis Cartilage 18 Suppl 3:S113-6). From the H & E staining of the subchondral bone area, all samples displayed normal bone morphology indicated by the darker pink stain with normal vascularization (FIG. 13, Panel B). In general, no visible difference regarding the subchondral structure was observed among all groups compared to the healthy control.

Figure 14:
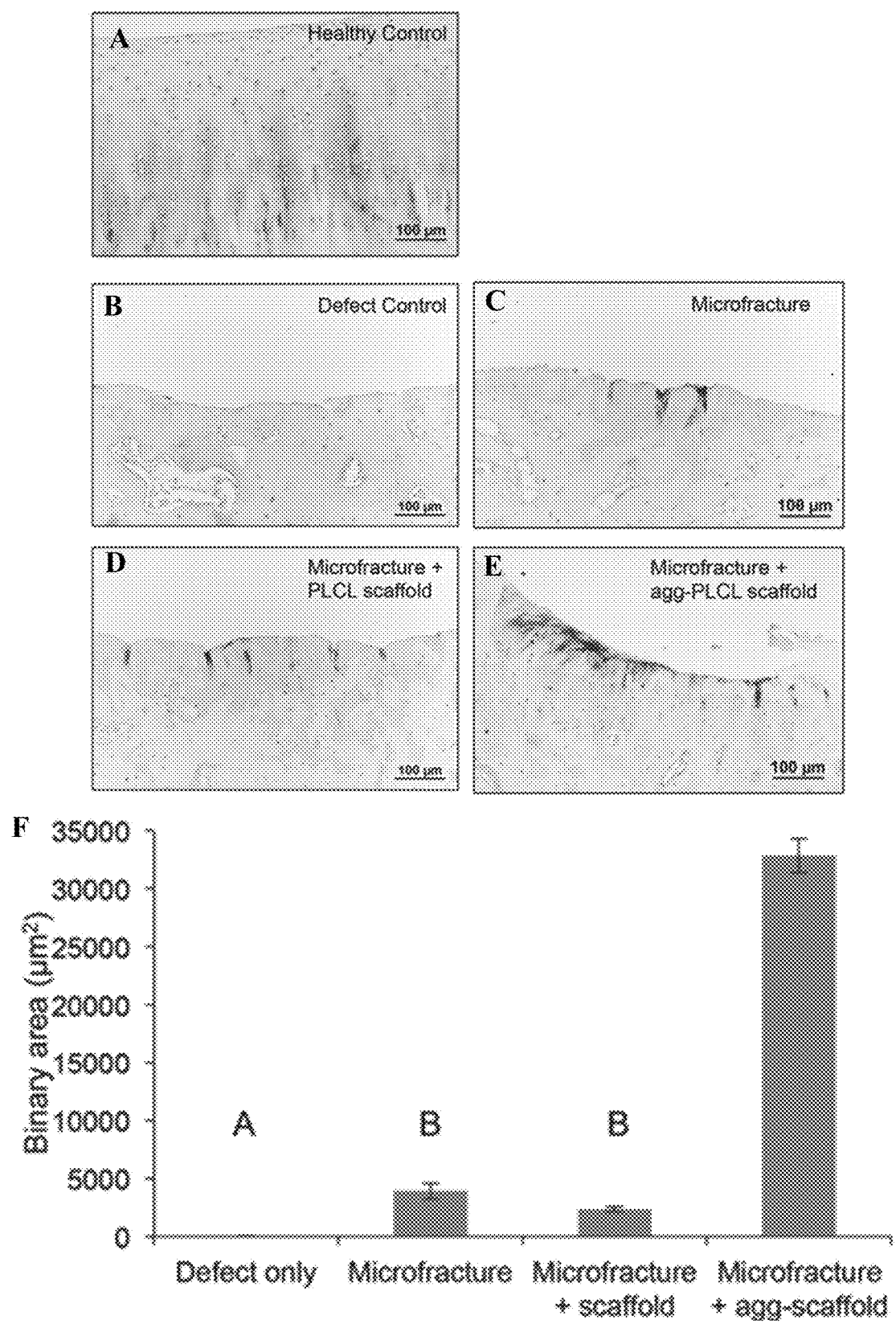
FIG. 14 shows images from immunohistochemistry staining of Type II collagen and quantification including: Healthy control group (Panel A); Defect control group (Panel B); Microfracture group (Panel C); Microfracture+PLCL scaffold group (Panel D); and Microfracture+Aggrecan-PLCL scaffold group (Panel E). The type II collagen was stained in brown (shown as dark gray/black). All experiment groups showed significantly higher type II collagen expression compared to the defect control. The addition of the aggrecan functionalized scaffold further increased the expression of type II collagen in the regenerated cartilage tissue. The level of expression in each group was quantified (Panel F). N=3. Data is shown as mean±standard deviation. ANOVA was performed to compare the significance among groups. Means that do not share the same letter are significantly different.

A major concern of microfracture is the variance in success among cases because the released MSCs and biomolecules have limited guidance and support in the defect area. The three rabbits in the microfracture group also showed relatively large standard deviations in multiple assessments. However, such variance is reduced by incorporating the aggrecan-PLCL scaffold, indicating the consistency of the treatment effect. To further evaluate the quality of the regenerated cartilage tissue, immunostaining of type II collagen was performed (FIG. 14). The calculated type II expression level as binary area were 59±12 $\mu m^2$, 3909±681 $\mu m^2$, 2358±214 $\mu m^2$, and 32886±1471 $\mu m^2$ for defect control group, microfracture group, microfracture with unmodified scaffold group, and microfracture with aggrecan scaffold group, respectively (FIG. 14, Panel F). All experimental groups displayed a significantly different expression level compared to the defect control from the quantitative analysis. As a comparison, the type II collagen presence, in terms of area in unit area, was approximately 10 times more compared to the microfracture treated group.

Example 3

3D Printed Interface Scaffolds for Cartilage Regeneration

A multilayer scaffold composed of poly(L-lactide-co-caprolactone) (PLCL) and amine end-capped poly(lactic-co-glycolic acid) (amine-PLGA) was successfully printed with high resolution. The disclosed approach creates a regenerative environment with a robust bone-cartilage interface within an osteochondral implant. It is believed that co-printing the architecture at the bone-cartilage interface improves the adhesion between the bone and cartilage layers by increasing the contact points between the print strands of the same mixture at the interface.

Figure 15:
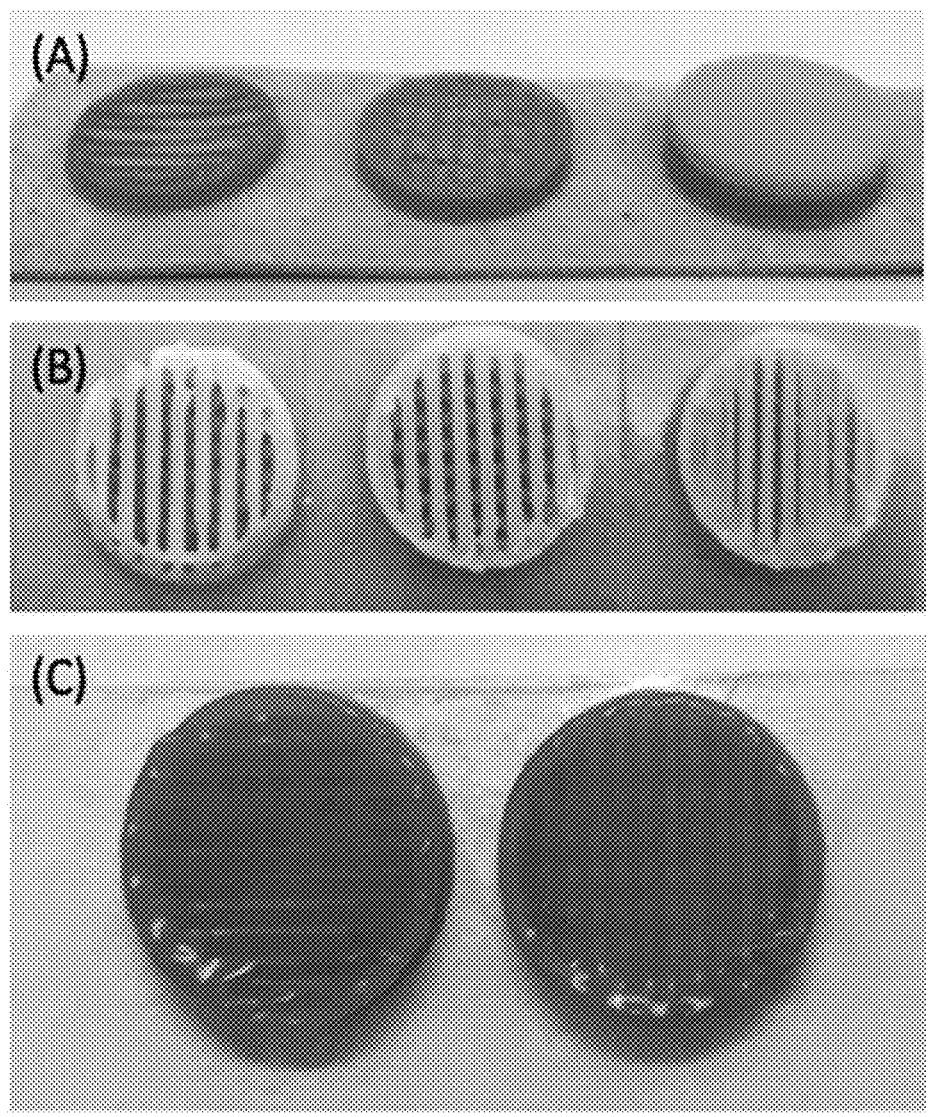
FIG. 15 shows images of osteochondral 3D printed osteochondral interface scaffolds in accordance with disclosed embodiments. Referring to Panel A, the cartilage strands (white) were printed alongside the bone strands (dark grey) at the interface. Referring to Panel B, the orientation and distance between the strands were adjusted to print the cartilage and bone strands adjacently. Panel C shows final interface scaffolds.

Preliminary experiments demonstrated the feasibility of interface printing via a 3D printing strategy (FIG. 15). A thermoplastic polymer mixture of PLCL and amine-PLGA (as described in Example 2 above) served as the chondral matrix, while polycaprolactone (PCL) served as the primary osteo matrix. Exemplary printing patterns of the bone and cartilage layers were explored. The interface layer may be co-printed with the two polymer formulations.

A 3D cylinder model with a dimension of 8.0 mm (diameter)×1.6 mm (height) were designed using SOLIDWORKS® software (Dassault Systémes, Vélizy-Villacoublay, France). A 0.4 mm inner diameter (ID) needle is used to print the scaffolds. According to the manufacturer's (EnvisionTEC, Gladbeck, Germany) instruction, the scaffold is sliced into layers with a slice thickness equal to 80% of the ID of the needle before printing. A second sliced 3D cylinder model is superimposed over the first cylinder model to establish the interface layer using BIOPLOTTER™ RP prototyping tool (EnvisionTEC, Gladbeck, Germany). The interface layer spans two print layers co-printed with the two polymer formulations (FIG. 15). The printing conditions may be adjusted for needle size, temperature, pressure, printing speed, fiber spacing and inner fiber pattern. The printing platform is maintained at 15° C.

Figure 16:
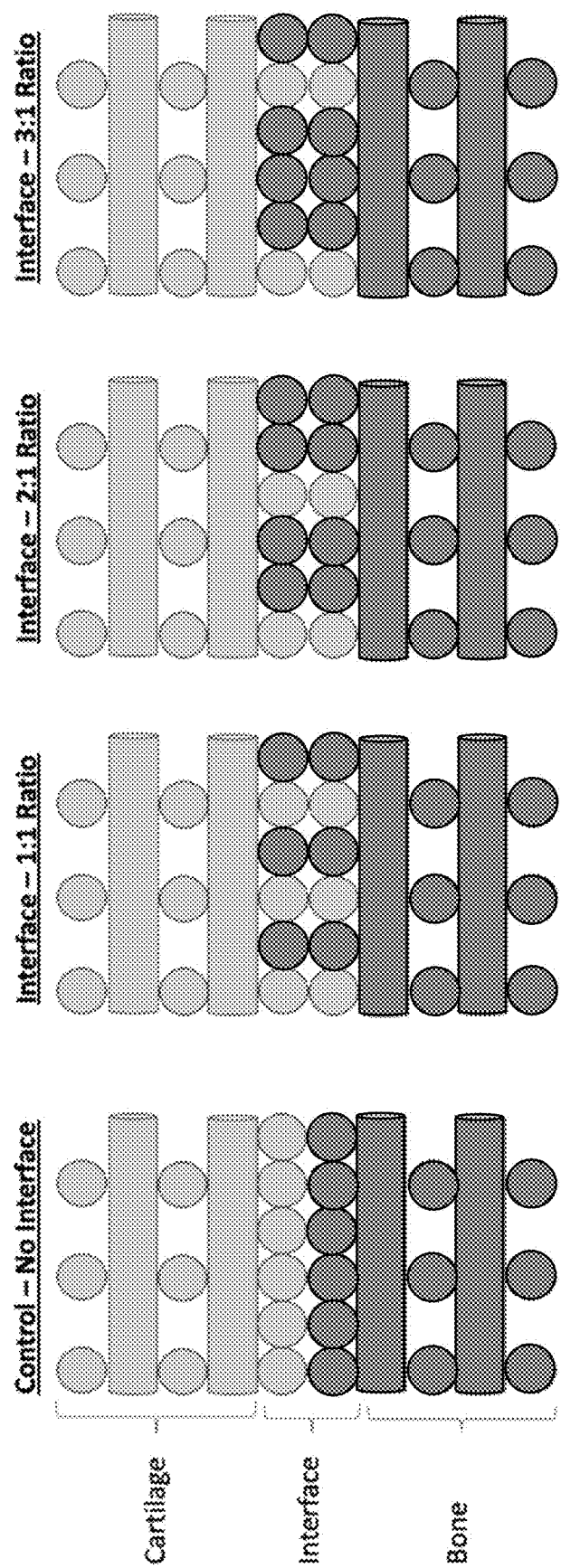
FIG. 16 illustrates schematically four osteochondral interface patterns in accordance with embodiments of the present disclosure. Depicted patterns include: i) control—no interface; ii) 1:1 bone to cartilage interface ratio; iii) 2:1 bone to cartilage interface ratio; and iv) 3:1 bone to cartilage interface ratio.

Four patterns for 3D printing fabrication were evaluated to assess the mechanical robustness at the osteochondral implant interface (FIG. 16). Exemplary scaffold and interface patterns included: i) control—no interface; ii) 1:1 bone to cartilage interface ratio; iii) 2:1 bone to cartilage interface ratio; and iv) 3:1 bone to cartilage interface ratio. The printing pattern of the bone and cartilage layers may be readily modified depending on the particular application. As shown, the interface layer is co-printed with the two polymer formulations. Thus, an acellular scaffold implant is provided that comprises: i) a cartilage layer (e.g., PLCL/PLGA layer, as described in Example 2 above); ii) a bone layer (e.g., PCL layer); and iii) an interlocking interface layer or membrane between the cartilage and bone layers composed of portions or strands of the cartilage layer material and bone layer material (see FIG. 11). Mechanical properties of the interface layer are determined via interfacial shear and compression tests.

CONCLUSIONS

An effective method to regenerate critical articular defects was developed by utilizing a 3D-printed bioactive scaffold in combination with microfracture surgery. The surface of the 3D-printed polymer scaffold was covalently modified with aggrecan to improve cell adherence and maintain cell function at the scaffold surface. With the functionalized scaffold, the microfracture outcome was significantly enhanced by providing extra support to the stem cells and growth factors released from bone marrow during the healing process. The additional aggrecan scaffold treatment resulted in a substantially thicker and healthier regenerated cartilage layer. The biofunctionalized acellular scaffold combined with microfracture is thus suitable for various clinical applications, and substantially improves current treatment strategies (e.g., microfracture procedures) without the need for additional surgeries and with a relatively low cost compared to cell-based therapies.

All identified publications and references mentioned in this specification are herein incorporated by reference to the same extent as if each individual publication was specifically and individually indicated to be incorporated by reference in its entirety. While the invention has been described in connection with exemplary embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the features hereinbefore set forth.

What is claimed is:

1. An implantable device comprising an acellular polymeric scaffold, wherein said acellular polymeric scaffold comprises PLCL-amine scaffold material that comprises a mixture of:
   (A) poly(L-lactide-co-caprolactone) (PLCL); and
   (B) an aggrecan—amine end capped poly(L-lactide-co-glycolic acid) (PLGA) conjugate, wherein said aggrecan is covalently bonded to said amine end capped PLGA via an amide bond.

2. The device of claim 1, wherein said scaffold is fabricated via three-dimensional (3D) printing.

3. The device of claim 2, wherein said 3D printing is material extrusion 3D printing.

4. The device of claim 1, wherein said scaffold comprises a first layer having a first fiber pattern, and a second layer having a second fiber pattern different from said first fiber pattern.

5. The device of claim 4, wherein said first fiber pattern comprises a plurality of spaced parallel fibers, and said second fiber pattern comprises a plurality of spaced parallel fibers.

6. The device of claim 5, wherein said plurality of spaced parallel fibers of said first fiber pattern are offset in plan view from said plurality of spaced parallel fibers of said second fiber pattern.

7. The device of claim 5, wherein said second fiber pattern comprises a generally crosshatch pattern in plan view.

8. The device of claim 5, wherein said scaffold comprise a third layer having a third fiber pattern different from said first and second fiber patterns.

9. The device of claim 8, wherein said third fiber pattern comprises a plurality of spaced parallel fibers, wherein said plurality of spaced parallel fibers of said third fiber pattern are generally perpendicular in plan view from said plurality of spaced parallel fibers of said first fiber pattern.

10. The device of claim 4, wherein said first layer has a first thickness, and said second layer has a second thickness at least about twice said first thickness.

* * * * *